US008652483B2

(12) United States Patent
Münch et al.

(10) Patent No.: US 8,652,483 B2
(45) Date of Patent: Feb. 18, 2014

(54) VIRAL INFECTION ENHANCING PEPTIDE

(75) Inventors: Jan Münch, Neu-Ulm (DE); Frank Kirchhoff, Ulm-Einsingen (DE); Maral Yolamanova, Ulm (DE)

(73) Assignees: Jan Münch, Neu-Ulm (DE); Frank Kirchhoff, Ulm-Einsingen (DE)

( * ) Notice: Subject to any disclaimer, the term of this patent is extended or adjusted under 35 U.S.C. 154(b) by 0 days.

(21) Appl. No.: 13/297,987

(22) Filed: Nov. 16, 2011

(65) Prior Publication Data

US 2012/0122177 A1 May 17, 2012

(30) Foreign Application Priority Data

Nov. 16, 2010 (EP) .................................... 10191316

(51) Int. Cl.
| | | |
|---|---|---|
| *A61K 39/00* | (2006.01) | |
| *C07K 5/00* | (2006.01) | |
| *C12Q 1/68* | (2006.01) | |
| *C12Q 1/70* | (2006.01) | |
| *C12N 9/00* | (2006.01) | |
| *C12N 7/00* | (2006.01) | |
| *A61K 39/21* | (2006.01) | |

(52) U.S. Cl.
USPC ................... 424/184.1; 424/207.1; 530/300; 530/395; 435/5; 435/174; 435/235.1

(58) Field of Classification Search
None
See application file for complete search history.

(56) References Cited

U.S. PATENT DOCUMENTS 6,042,836 A * 3/2000 Berman et al. ............. 424/208.1
2003/0235835 A1 12/2003 Alizon et al.

FOREIGN PATENT DOCUMENTS

| WO | WO 9104273 A | * | 4/1991 |
| WO | WO 9428929 A | * | 12/1994 |
| WO | 99/48925 A1 | | 9/1999 |
| WO | 01/24810 A1 | | 4/2001 |

OTHER PUBLICATIONS

Dey AK, David KB, Ray N, Ketas TJ, Klasse PJ, Doms RW, Moore JP. N-terminal substitutions in HIV-1 gp41 reduce the expression of non-trimeric envelope glycoproteins on the virus. Virology. Mar. 1, 2008;372(1):187-200. Epub Nov. 26, 2007.*
van Dam RM, Quake SR. Gene expression analysis with universal n-mer arrays. Genome Res. Jan. 2002;12(1):145-52.*
HIV Molecular Immunology 2009, Eds: Yusim K, Korber BTM, Brander C, Haynes BF, Koup R, Moore JP, Walker BD, and Watkins DI. Publisher: Los Alamos National Laboratory, Theoretical Biology and Biophysics, Los Alamos, New Mexico. LA-UR 09-05941. hiv.lanl.gov/content/immunology.*
Koup RA et.al. Priming immunization with DNA augments immunogenicity of recombinant adenoviral vectors for both HIV-1 specific antibody and T-cell responses. PLoS One. Feb. 2, 2010;5(2):e9015.*
Frey A, Neutra MR, Robey FA. Peptomer aluminum oxide nanoparticle conjugates as systemic and mucosal vaccine candidates: synthesis and characterization of a conjugate derived from the C4 domain of HIV-1MN gp120. Bioconjug Chem. May-Jun. 1997;8(3):424-33.*
Easterhoff D, DiMaio JT, Doran TM, Dewhurst S, Nilsson BL. Enhancement of HIV-1 infectivity by simple, self-assembling modular peptides. Biophys J. Mar. 2, 2011;100(5):1325-34.*
Loksztejn A, Dzwolak W. Noncooperative dimethyl sulfoxide-induced dissection of insulin fibrils: toward soluble building blocks of amyloid. Biochemistry. Jun. 9, 2009;48(22):4846-51.*
Kim KA, Yolamanova M, Zirafi O, Roan NR, Staendker L, Forssmann WG, Burgener A, Dejucq-Rainsford N, Hahn BH, Shaw GM, Greene WC, Kirchhoff F, Münch J. Semen-mediated enhancement of HIV infection is donor-dependent and correlates with the levels of SEVI. Retrovirology. Jun. 23, 2010;7:55.*
Yolamanova M, et. al. Peptide nanofibrils boost retroviral gene transfer and provide a rapid means for concentrating viruses. Nat Nanotechnol. Feb. 2013;8(2):130-6. Epub Jan. 20, 2013.*
Levy M, Garmy N, Gazit E, Fantini J. The minimal amyloid-forming fragment of the islet amyloid polypeptide is a glycolipid-binding domain. FEBS J. Dec. 2006;273(24):5724-35. Erratum in: FEBS J. Apr. 2007;274(7):1878.*
Brender, J.R., et al., "An α-Helical Conformation of the SEVI Peptide, a Dramatic Enhancer of HIV Infectivity, Promotes Lipid Aggregation and Fusion", Biophysical Journal, (2009), vol. 97, No. 9, pp. 2474-2483.
Gurgo, C., et al., "Envelope sequences of two new United States HIV-1 isolates", Virology, (1988), vol. 164, No. 2, pp. 531-536.
Münch, J., et al., "Semen derived amyloid fibrils drastically enhance HIV infection", Cell, (2007), vol. 131, No. 6, pp. 1059-1071.
Papkalla, A., et al., "Nef Enhances Human Immunodeficiency Virus Type 1 Infectivity and Replication Independently of Viral Coreceptor Tropism", Journal of Virology, (2002), vol. 76, No. 16, pp. 8455-8459.
Roan, N.R., et al., "The Cationic Properties of SEVI Underlie Its Ability to Enhance Human Immunodeficiency Virus Infection", Journal of Virology, (2009), vol. 83, No. 1, pp. 73-80.
Roan, N.R., et al., "Aminoquinoline Surfen Inhibits the Action of SEVI (Semen-derived Enhancer of Viral Infection", Journal of Biological Chemistry, (2010), vol. 285, No. 3, pp. 1861-1869.
Wurm, M., et al., "The influence of semen-derived enhancer of virus infection on the efficiency of retroviral gene transfer", Journal of Gene Medicine, (2010), vol. 12, pp. 137-146.
Extended European Search Report, completed on Apr. 19, 2011, seven pages.

* cited by examiner

Primary Examiner — Benjamin P Blumel
Assistant Examiner — Rachel Gill
(74) Attorney, Agent, or Firm — Nath, Goldberg & Meyer; Tanya E. Harkins

(57) ABSTRACT

The invention relates to a peptide derived from HIV-1 gp120 which forms insoluble aggregates when introduced into an aqueous solution and its use for enhancing viral infection of cells. In addition, the invention comprises methods for enhancing viral infection of cells, for concentrating a virus and for separating a virus from a fluid.

12 Claims, 31 Drawing Sheets

A

| SEQ ID NO. | SW-PEPTIDE | SEQUENCE | Length (aa) | MW (Da) | pI | Positions cor. to gp120 (aa) |
|---|---|---|---|---|---|---|
| 13 | Gp120* | SNNNITIQCKIKQIINMWQEVGKAMYAPPISG | | | | 410-441 |
| 1 | SWB | QCKIKQIINMWQ | 12 | 1533,8 | 9,31 | 417-428 |
| 2 | SWE | QCKIKQIINMW | 11 | 1404,7 | 9,31 | 417-427 |
| 3 | SW1010 | NITIQCKIKQIINMWQEVG | 19 | 2258,7 | 8,20 | 413-431 |
| 4 | SW1014 | QIINMWQEVG | 10 | 1217,4 | 4,00 | 422-431 |
| 5 | SWNL43 | YITLPCRIKQFINMWQEVG | 19 | 2277,7 | 7,89 | |
| 6 | Core4aa | INMW | | | | |
| 7 | Core6aa | QKINMW | | | | |
| 8 | SWA | NITIQCKIK | 9 | 1060,3 | 9,31 | 413-421 |
| 9 | SWD | QCKIKQ | 6 | 746,9 | 9,31 | 417-422 |
| 10 | SWF | KIK | 3 | 387,8 | nd | 419-421 |
| 11 | SWC | KIKQIINMWQ | 10 | 1301,6 | 10,00 | 419-428 |
| 12 | SWCON | YITLPCRIKQIINMWQVG | 19 | 2171,6 | 9,58 | |

* Aa 410-441 Accession No.: AAA44867

VIRAL INFECTION ENHANCING PEPTIDE

FIELD OF THE INVENTION

The present invention relates to a peptide derived from Human Immunodeficiency Virus-1 (HIV-1) glycoprotein (gp) 120, which forms insoluble aggregates when introduced into an aqueous solution and to certain uses thereof. In addition, the invention relates to methods for enhancing viral infection of cells, for concentrating viruses and for separating viruses from fluids.

The Sequence Listing submitted in text format (.txt) on Jan. 31, 2012, named "SequenceListing_ST25.txt", (created on Monday, Jan. 30, 2012, 3.92 KB), is incorporated herein by reference.

BACKGROUND OF THE INVENTION

Using viral vectors to introduce foreign deoxyribonucleic acid (DNA) into a eukaryotic cell is a well-established technique in the fields of biotechnology, life science research and gene therapy. However, whether foreign DNA is successfully introduced into a cell highly depends on the efficiency of the viral infection/transduction which in turn is influenced by various parameters such as the type of virus and cell. To increase infection efficiency, additives are used, as for example recombinant human fibronectin fragment CH-2961 so-called RetroNectin® (Takara; TAK T100). RetroNectin® recombinant human fibronectin fragment is a chimeric peptide of recombinant human fibronectin fragments produced in E. coli. It contains 574 amino acids with a molecular weight of 63 kDa. When coated on the surface of cell culture chambers such as culture dishes, petri dishes, flasks or bags, RetroNectin® recombinant human fibronectin fragment enhances retrovirus-mediated gene transduction into mammalian cells. This enhancement is thought to be due to co-localization of retroviral particles and target cells at the site of RetroNectin® recombinant human fibronectin fragment. RetroNectin® recombinant human fibronectin fragment binds to virus particles via interaction with the heparin-binding domain II, and to cells mainly through interaction of the cell surface integrin receptor Very Late Antigen-4 (VLA-4) with the fibronectin Connecting Segment 1 peptide (CS1) site. Additionally, cells may also bind through the interaction of another fibronectin ligand within the central cell-binding domain with a corresponding integrin receptor Very Late Antigen-5 (VLA-5) on the cell surface.

The production of RetroNectin® recombinant human fibronectin fragment is elaborate and cost intensive, since the artificial protein is relatively large. In addition, it has to be coated on culture dishes, making the application time and labour intensive. Moreover, RetroNectin® recombinant human fibronectin fragment can not be applied to improve infection of those types of cells, as e.g. some kind of stem cells, which immediately start to differentiate upon plating and thus have to be kept in suspension.

An alternative approach for supporting viral infection of cells was suggested after the discovery that HIV infection in vivo is supported by semen. The infection supporting properties could be attributed to a 38 amino acid fragment of prostatic acidic phosphatase (PAP248-286) which was named semen-derived enhancer of virus infection (SEVI) (Münch et al., 2007). SEVI was shown to support viral infection in vitro probably due to forming amyloid fibrils, which are thought to interact with both, the viral envelope and the cell membrane (Brender et al., 2009). Although SEVI displays viral infection supporting properties, its technical applicability is rather limited. The lyophilized fragments of prostatic acidic phosphatase (PAP) have to be dissolved in solutions of neutral pH and distinct salt concentrations and must be agitated at 37° C. for about 1 to 3 days (Münch et al., 2007, Roan et al., 2009, Roan et al., 2010). Thus, SEVI is not suitable for use in high throughput biotechnological or life science applications. Therefore, novel means and methods are required to efficiently enhance viral infection of cells, which are easy and inexpensive to provide and convenient to apply.

SUMMARY OF THE INVENTION

In a first aspect the present invention relates to a peptide derived from HIV-1 gp120 with at least 4 to about 25 amino acids, wherein the peptide forms insoluble aggregates when introduced into an aqueous solution and the peptide comprises a sequence selected from the group consisting of SEQ ID NO: 1, 2, 3, 4, 5, 6, 7, 11 and 12.

In a further aspect, the invention relates to a kit comprising a viral infection enhancing peptide of gp120.

In a further aspect the invention relates to an in vitro method for enhancing viral infection of cells comprising the steps of providing a viral infection enhancing peptide dissolved in an organic solvent, introducing the peptide into an aqueous solution to obtain a solution comprising insoluble aggregates of the peptide, mixing the solution with the cells and a virus, and culturing the cells, wherein the number of infected cells is increased compared to the number of infected cells in a virus only control.

In a further aspect the present invention relates to an in vitro method for concentrating a virus comprising the steps of providing a viral infection enhancing peptide dissolved in an organic solvent, introducing the peptide into an aqueous solution to obtain a solution comprising insoluble aggregates of the peptide, adding the solution to a fluid comprising the virus, centrifuging the fluid at about 2000 to 25000 g, and collecting a pellet, wherein the virus is concentrated in the pellet.

In a further aspect the present invention relates to the use of a peptide comprising a sequence selected from the group consisting of SEQ ID NO: 1, 2, 3, 4, 5, 6, 7, 11 and 12 for enhancing infection of a cell with a virus in vitro.

In a further aspect the invention relates to the use of a peptide comprising a sequence selected from the group consisting of SEQ ID NO: 1, 2, 3, 4, 5, 6, 7, 11 and 12 for binding a virus to a carrier by coating the carrier with the peptide.

DETAILED DESCRIPTION OF THE INVENTION

Figure 1:
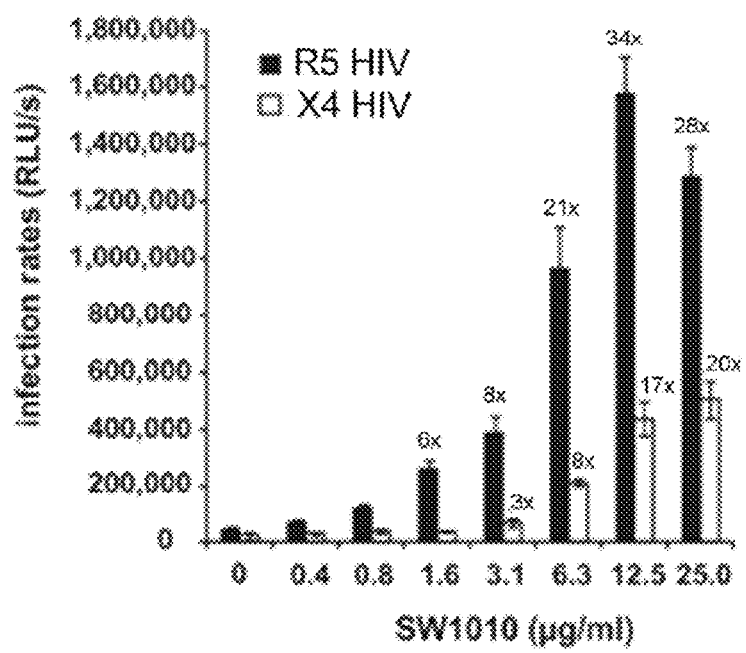
FIG. 1: Table displaying sequences, physical and chemical parameters of peptides derived from gp120 of HIV-1 (SW-peptides) (A). SW1010 enhanced infection of TZM-bl cells by R5 HIV-1 and X4 HIV-1 in a concentration depending manner (B). Electron microscopy images of insoluble material of SW1010 and SWB (C). SW1010 and SWB solutions reacted with Thioflavin T (ThT) (D) and CongoRed (E) indicating formation of amyloid like material. SWB enhanced virus infection more efficiently than SW1010 (F).
Figure 1:
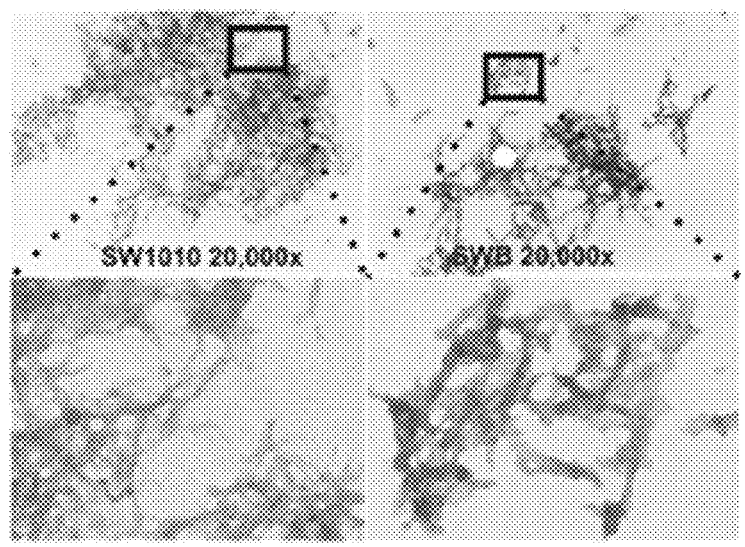
Figure 1:
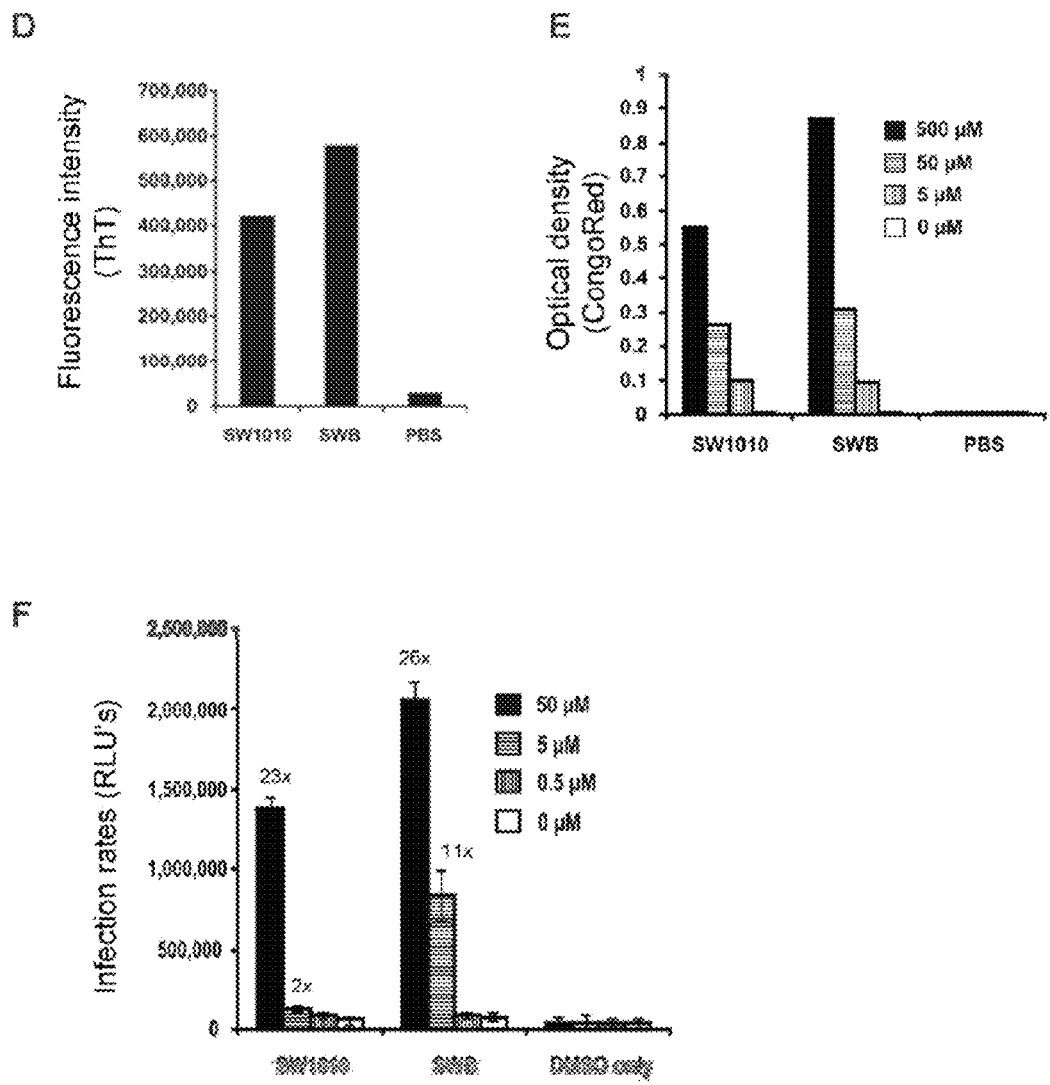

In a first aspect, the present invention relates to a peptide derived from HIV-1 gp120 with at least 4 to about 25 amino acids, wherein the peptide forms insoluble aggregates when introduced into an aqueous solution and the peptide comprises a sequence selected from the group consisting of SEQ ID NO: 1, 2, 3, 4, 5, 6, 7, 11 and 12.

The term "peptide" as used herein refers to an organic compound of at least 2 amino acids linked by a peptide bond and comprises peptides, oligopeptides and proteins, independently of their structure or sequence. The term equally refers to naturally occurring peptides, artificial peptides and to peptides obtained by chemical synthesis or biosynthesis. The peptides disclosed herein (SW-peptides) are derived from the peptide gp120 of HIV-1 strain MN (Gurgo et al. 1988) (FIG. 1A). gp120 together with gp41 arises by proteolytic cleavage of the precursor protein gp160, which is encoded by the envelope (env) gene of HIV-1. Within the virus particle, gp120 is localized at the outer surface of the virus where it interacts with the membrane of the host cell thereby mediating infection.

The inventors surprisingly found that certain peptides, derived from the beta 19 and beta 20 strands located adjacent to the third variable (V3) loop of gp120 (amino acids 410-441 of gp120, SEQ ID NO: 13) (henceforth referred to as viral infection enhancing peptides of gp120), form insoluble aggregates when introduced into an aqueous solution. These aggregates display distinct and unexpected biochemical properties as they are able to interact with viral particles and increase viral infectivity.

In a preferred embodiment the peptide derived from HIV-1 gp120 comprises SEQ ID NO: 8. This peptide is derived from SW1010 and shares several properties with the sequences SEQ ID NO: 1, 2, 3, 4, 5, 6, 7, 11 and 12. In particular, it shows strong infectivity enhancing activity.

In a preferred embodiment, the peptide consists of at least 4 amino acids to about 25, preferably about 20, more preferred about 15, most preferred 10 amino acids comprising the sequence Ile-Asn-Met-Trp (INMW, SEQ ID NO: 6). Viral infection enhancing peptides of gp120 comprising SEQ ID NO: 6 display aggregate forming and infection enhancing properties.

In another preferred embodiment, the peptide consists of at least 6 amino acids to about 25, preferably about 20, more preferred about 15, most preferred 10 amino acids comprising the sequence Gln-X-11e-Asn-Met-Trp (QXINMW, SEQ ID NO: 7), wherein X is any amino acid, preferably phenylalanine (Phe, F) or isoleucin (I, Ile). Peptides of 4 to 25 amino acids are comparatively short and thus fast and inexpensive to produce.

In another preferred embodiment the peptide consists of at least 10 to about 25 amino acids, preferably of at least 10 to about 20 amino acids and the sequence is selected from the group consisting of SEQ ID NO: 1, 2, 3, 4, 5, 11 and 12. SW1010 (SEQ ID NO: 3) corresponds to the beta 19 and beta 20 strands of the gp120 of HIV-1 MN strain, with SW1014 (SEQ ID NO: 4) representing the N-terminal half of SW1010. The peptides SWB (SEQ ID NO: 1), SWE (SEQ ID NO: 2) and SWC (SEQ ID NO: 11) represent variants of SW1010 of different length. The peptide SWNL43 (SEQ ID NO: 5) corresponds to SW1010 of the HIV-1 clone NL4-3. The peptide SWOON (SEQ ID NO: 12) is derived from a homologous consensus sequence of all HIV-1 M strains.

In another preferred embodiment the peptide comprises at least one positively charged amino acid, preferably arginine (R) or lysine (K). The presence of positively charged amino acids enhances the interaction between the peptide aggregates and the virus, thereby positively influencing the infection enhancing activity of the peptide.

In another preferred embodiment the peptide consists of at least 12 to about 25 amino acids comprising the sequence SWB (SEQ ID NO: 1). SWB particularly efficiently interacts with virus particles and enhances infection of several different types of cells.

Figure 2:
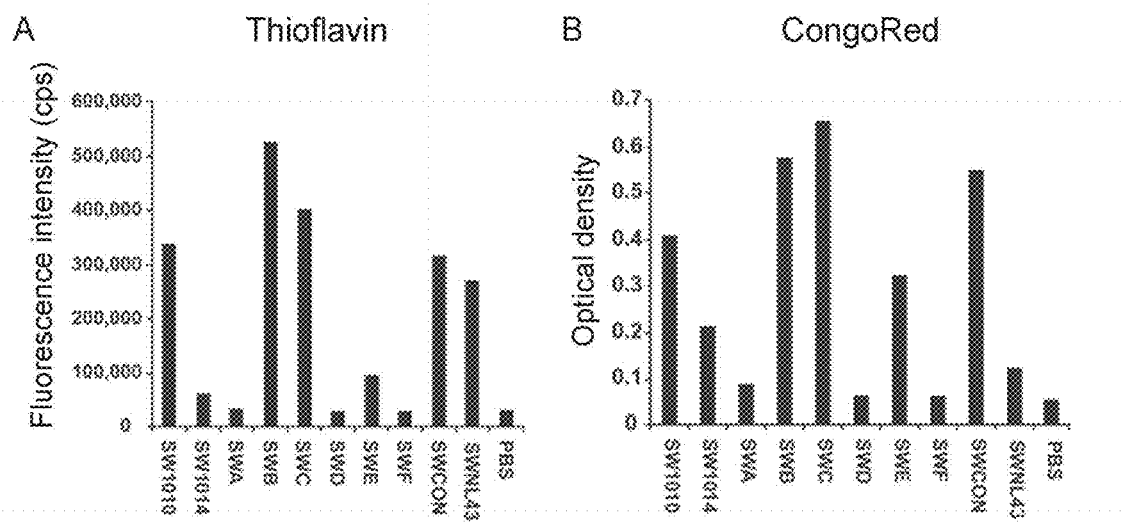
FIG. 2: Upon diluting dimethylsulfoxide (DMSO) stock solutions in phosphate buffered saline (PBS), SW1010 derivatives formed amyloid like material, reacting with Thioflavin T (A) and CongoRed (B).

The viral infection enhancing peptide forms insoluble aggregates when introduced into an aqueous solution (FIG. 1C). The term "aggregate" as used herein refers to an accumulation of peptides formed by chemical interactions including polymerization, non-covalent polymerization and/or hydrophobic association. The term includes fibrous structures, net-like structures as well as amyloid-like deposits. The aggregates formed by the peptide show several amyloid-like properties (FIG. 1 C, FIG. 2). Therefore, in a preferred embodiment, the insoluble aggregates of the peptide are detectable by an amyloid specific dye, preferably by Thioflavin T and/or Congo Red.

In a preferred embodiment the peptide immediately forms spontaneous insoluble aggregates within less than 10 seconds, preferably within about 0.5 to 10 seconds after introduction into the aqueous solution. Immediately upon introduction in the aqueous solution, the peptides are able to interact with viral particles and to enhance viral infection, such that they are right away available for further applications. Thus, time and work consuming preparations, as e.g. needed for providing SEVI, are not necessary.

In a preferred embodiment the aqueous solution is selected from the group consisting of phosphate buffered saline (PBS), $H_2O$ and cell culture medium. The term "aqueous solution" as used herein refers to polar and hydrophilic solutions based on water, comprising $H_2O$, $H_2O$ based solutions of any salt, saline, PBS, and cell culture mediums such as Dulbecco's Modified Eagle Medium (DMEM), Roswell Park Memorial Institute (RPMI) medium, F12 medium or basal medium. Since the peptides form aggregates in any aqueous solutions (FIG. 3), the solution can be selected according to the specific requirements of a biotechnological or experimental application. For example, the peptide may be introduced into $H_2O$ for reasons of purity or into PBS in case the experimental embodiment is particularly susceptible to osmotic changes. It also may be introduced in media selected according to the cell type to be infected by the virus.

Figure 5:
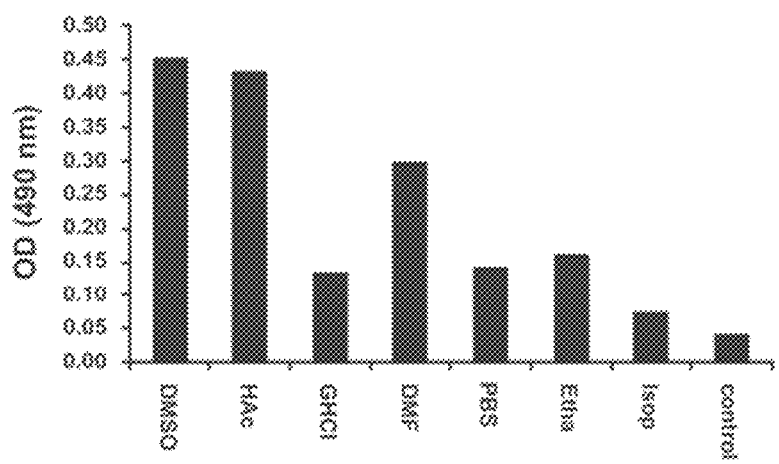
FIG. 5: Reactivity of PBS dilutions of SWB dissolved in dimethylsulfoxide (DMSO), acetic acid (HAc), guanidine hydrochloride (GHCl), dimethylformamide (DMF), phosphate buffered saline (PBS), ethanol (Etha) and isopropanol (Isop) with CongoRed (A). The efficiency of the infection enhancing effect of these SWB dilutions was influenced by the type of organic solvent (TZM-bl cells infected by R5 HIV) (B). Infection enhancing properties of SWB did not depend on the concentration of SWB in the solvent (TZM-bl cells infected by R5 HIV) (C). Infection enhancing properties of SWB were not altered by storage at 4° C. or -20° C. (TZM-bl cells infected by R5 HIV) (D).
Figure 5:
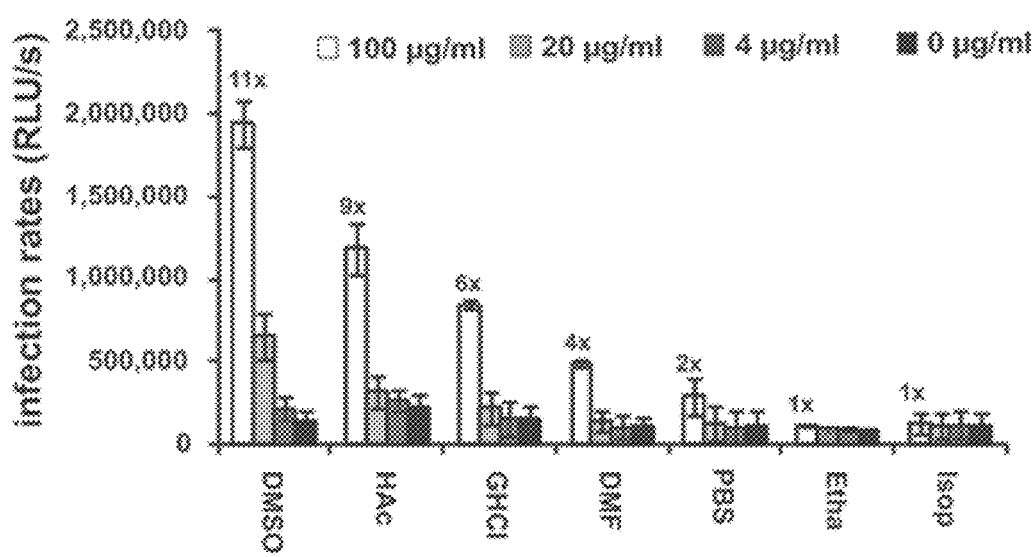
Figure 5:
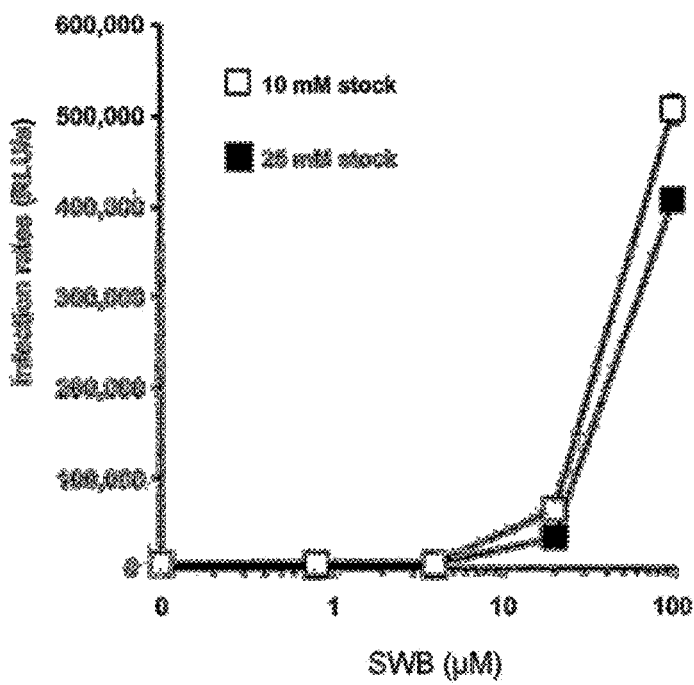
Figure 5:
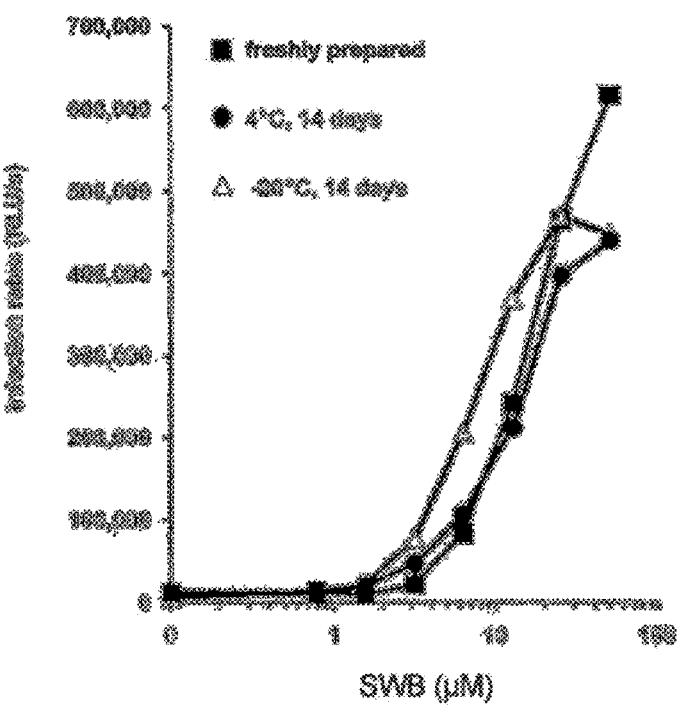

In a preferred embodiment the peptide is soluble in an organic solvent, preferably in an organic solvent comprising an organosulfur compound, more preferred in dimethylsulfoxide (DMSO). Dissolving the peptide in DMSO prior to introduction into the aqueous solution additionally promotes the formation of insoluble aggregates. In addition, the peptide can be stored in DMSO as well as in dilutions of DMSO stocks in PBS, without losing its infection enhancing properties (FIG. 5). Besides DMSO, particularly pure peptides are also soluble in $H_2O$. Thus, for peptides which have been subjected to high purification protocols after production, $H_2O$ is a preferred solvent.

In a preferred embodiment the peptide is biocompatible. The term "biocompatible" as used herein describes that a compound is non-toxic, does not negatively influences the metabolic activity of a cell and shows no significant influence on the performance of a cell. Since the peptide does not impair the metabolic activity of cells (FIG. 4 A, B) it may remain in the cell culture after infection such that additional washing steps to remove the peptide are not necessary. This reduces labor costs and circumvents additional stress to the cells.

In a further aspect, the invention relates to a nucleic acid molecule encoding a viral infection enhancing peptide of gp120. By way of the nucleic acid the peptide can be biotechnical produced, e.g. in cell systems such as *E. coli* or *C. cervisiae*.

In a further aspect, the invention relates to a vector comprising a nucleic acid molecule encoding a viral infection enhancing peptide of gp120. The vector may be chosen according to the production system for biotechnically producing the peptide.

In a further aspect, the invention relates to a kit comprising a viral infection enhancing peptide of gp120. According to the customer's needs, the kit may provide the peptide dissolved in DMSO or already introduced in an aqueous solution ready to use.

In a further aspect, the invention relates to an in vitro method for enhancing viral infection of cells comprising the steps of
a) providing a viral infection enhancing peptide of gp120 dissolved in an organic solvent,
b) introducing the peptide into an aqueous solution to obtain a solution comprising insoluble aggregates of the peptide,
c) mixing the solution with the cells and a virus, and
d) culturing the cells,
wherein the number of infected cells is increased compared to the number of infected cells in a virus only control.

Figure 6:
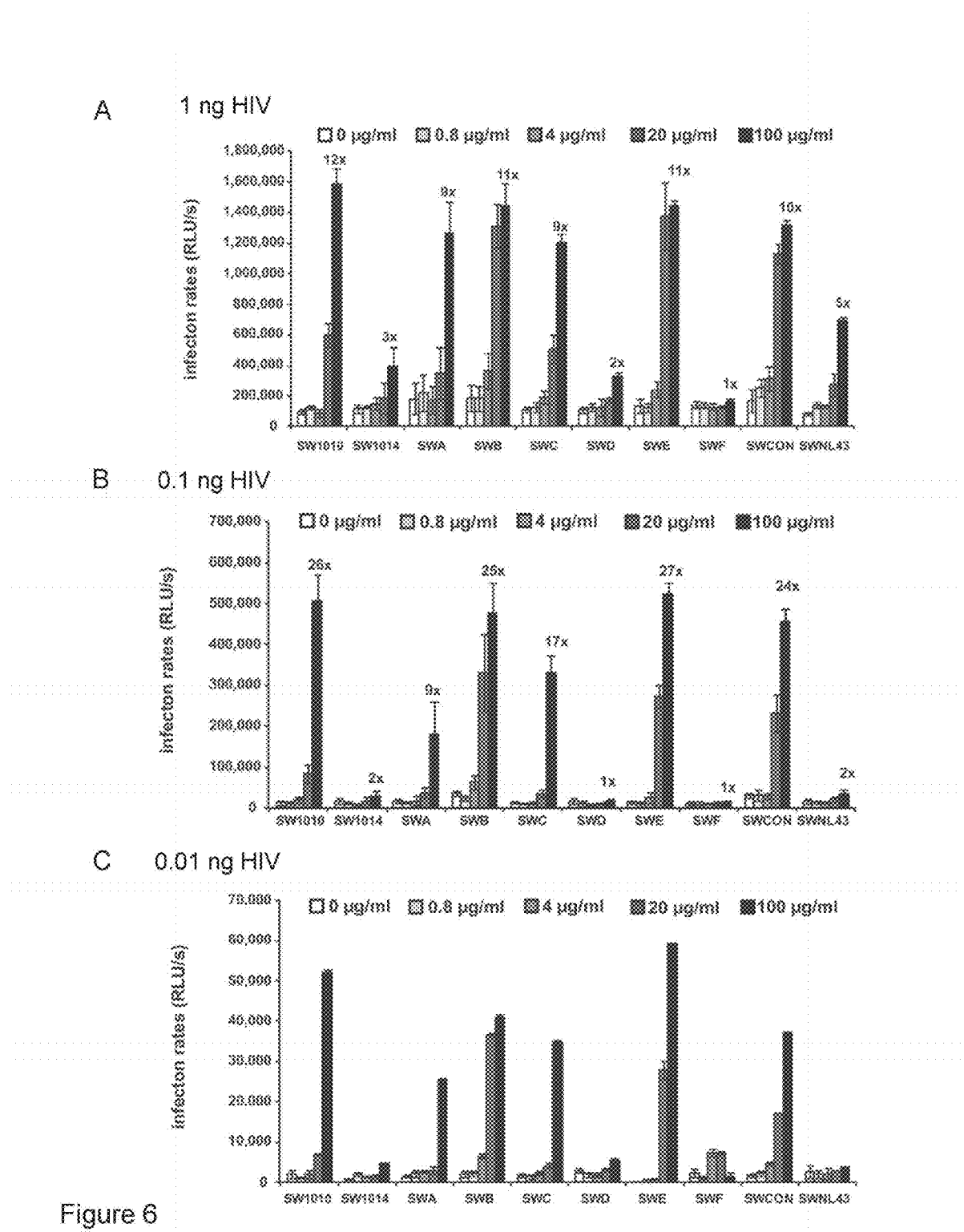
FIG. 6: The infection of TZM-bl cells by 1 ng (A), 0.1 ng (B) as well as 0.01 ng (C) R5 HIV-1 was enhanced by the presence of viral infection enhancing peptides of gp120. SWB improved HIV infection more efficiently compared to SEVI when mixed with 0.1 ng (D) as well as 0.01 ng (E) p24 antigen of an R5 tropic HIV-1.
Figure 6:
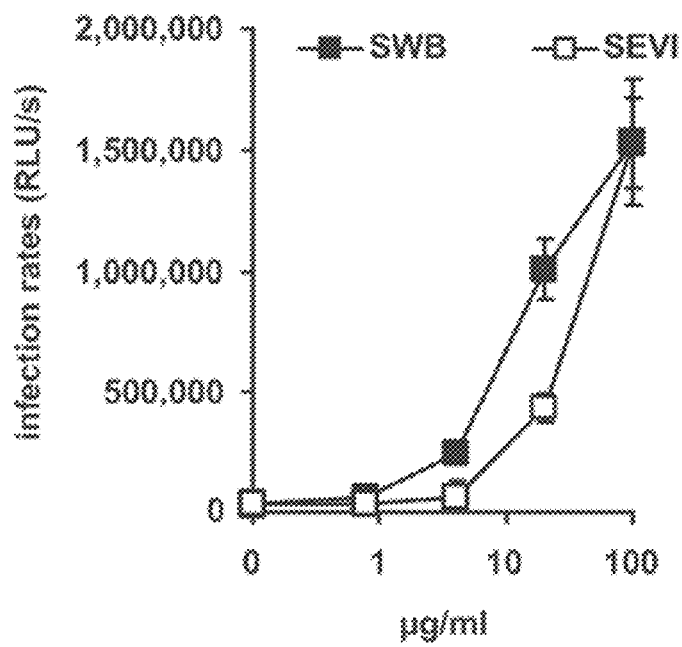
Figure 6:
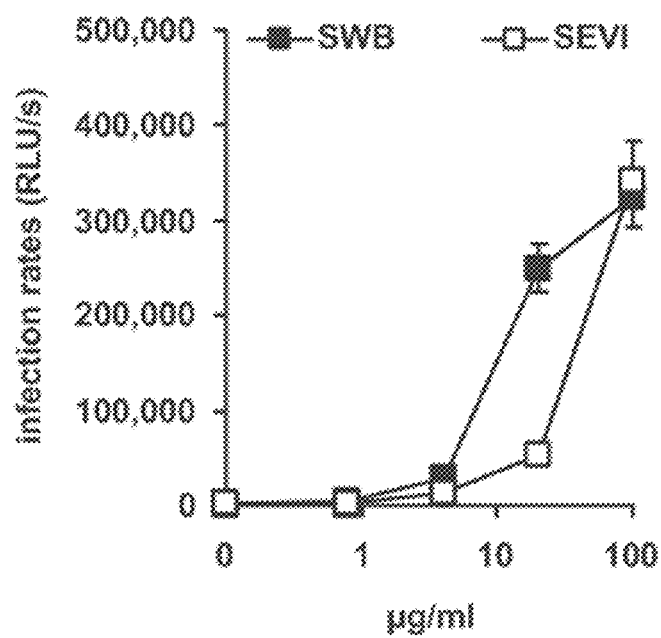
Figure 9:
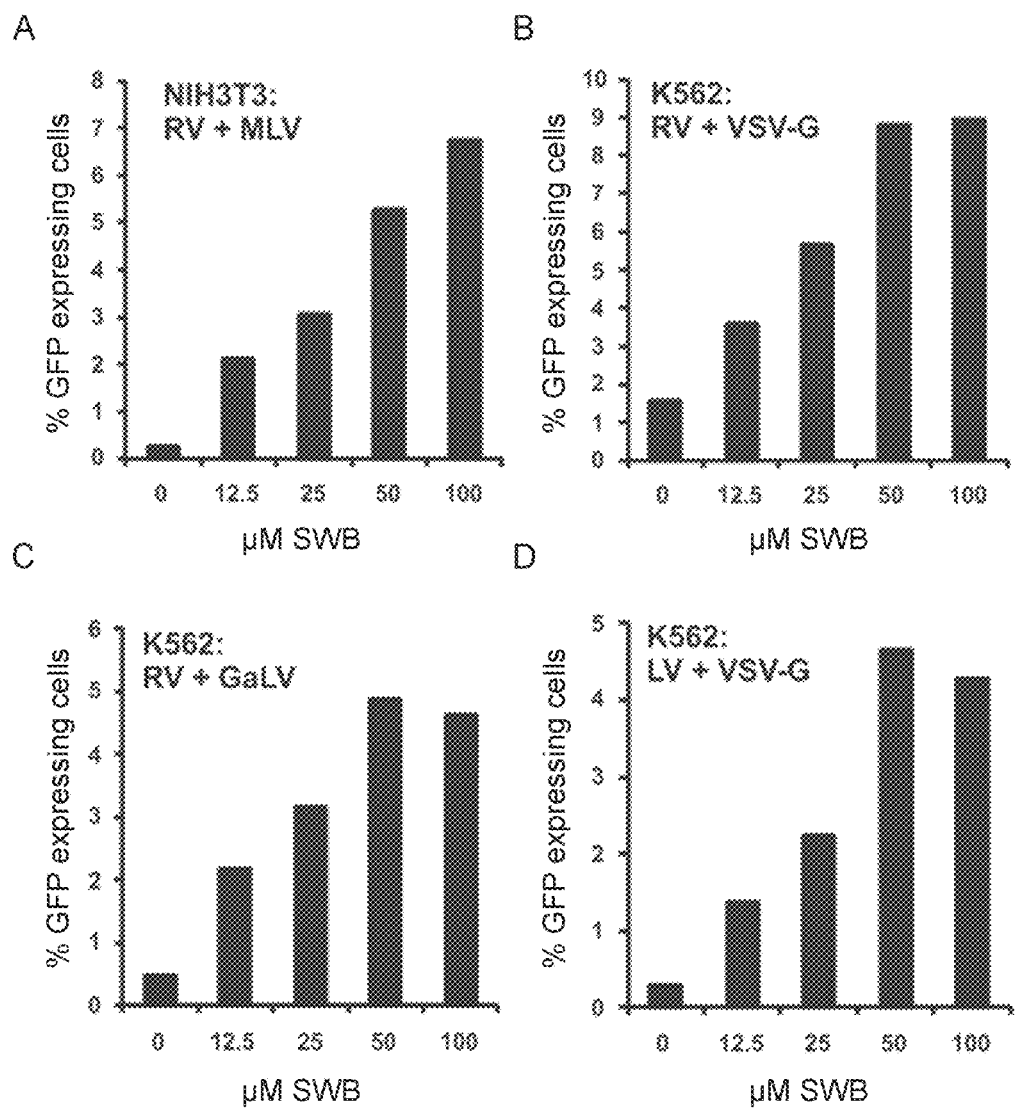
FIG. 9: SWB enhanced infection of murine (NIH3T3) and human (K562) cells by retroviral and lentiviral vectors pseudotyped with murine leukemia virus (MLV), vesicular stomatitis Indiana virus-G (VSV-G), and GaLV (A, B, C, D). SWB enhanced infection of 293 T cells by retroviral vectors pseudotyped with different glycoproteins (E). SWB enhanced infection of 293 T cells with lentiviral vectors pseudotyped with different glycoproteins (F). SWB accelerated viral gene expression in HeLa cells infected by GaLV gp (G, H) and VSV-G (I, K) retroviral vectors.
Figure 9:
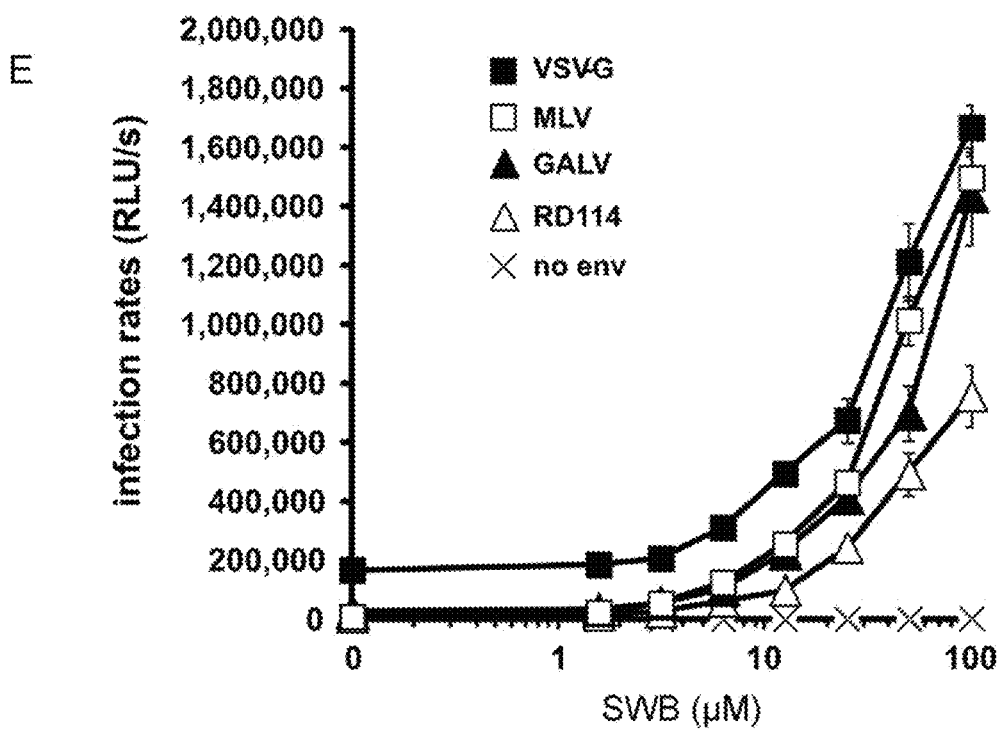
Figure 9:
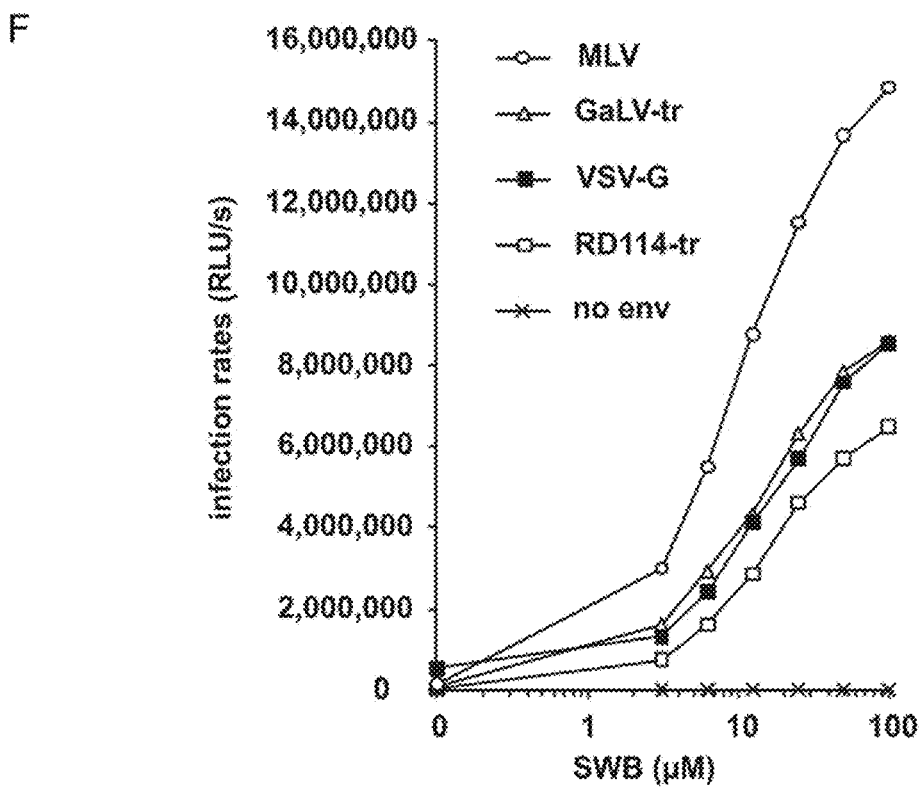
Figure 9:
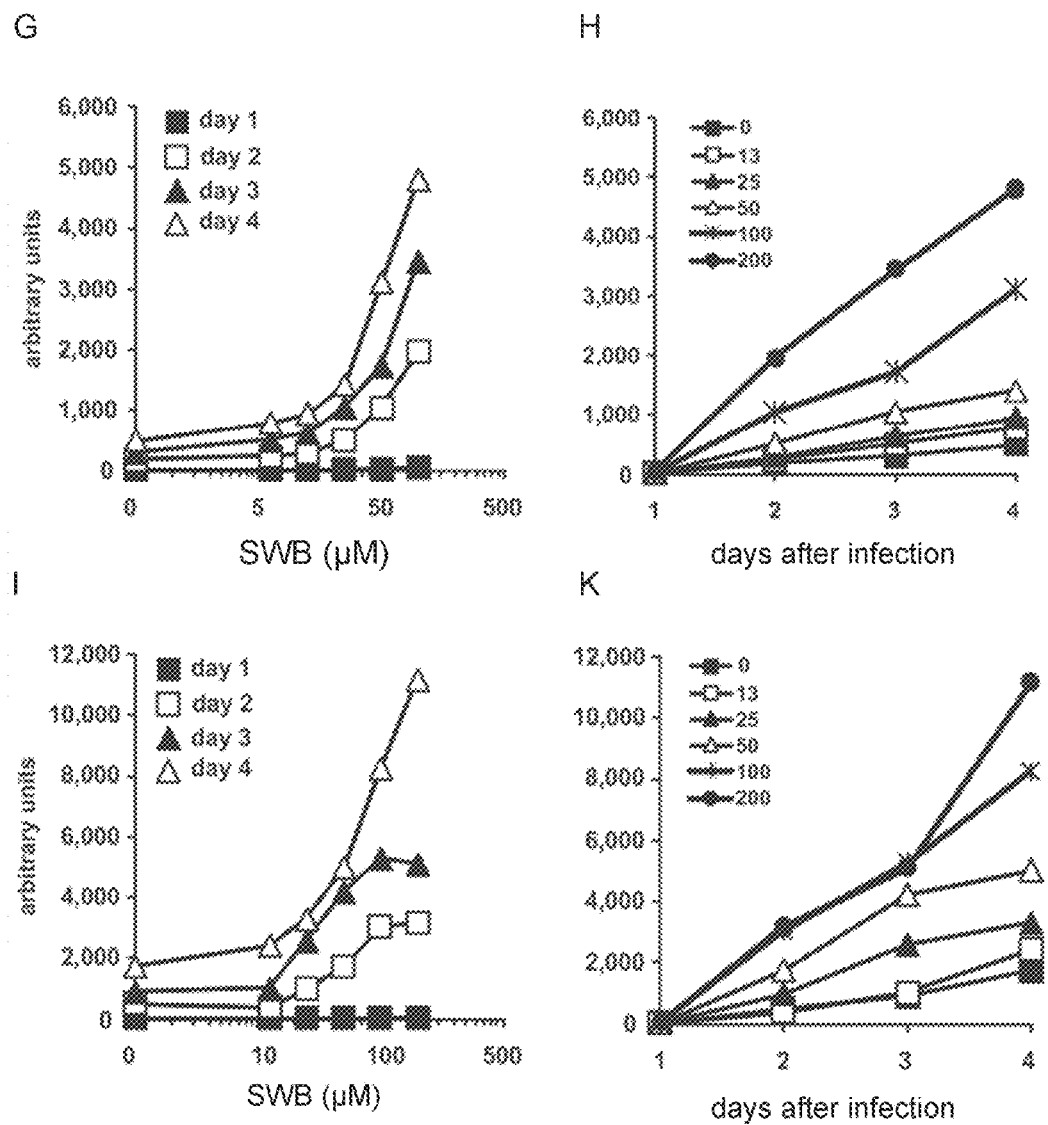
Figure 10:
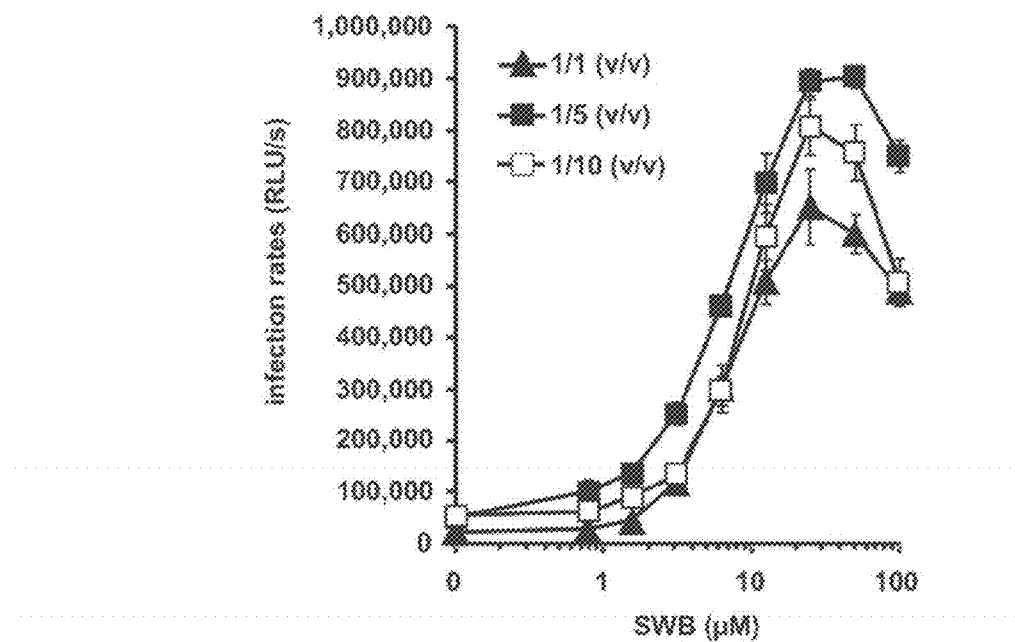
FIG. 10: Infection of TZM-bl cells by R5 HIV mixed with various volumes of SWB (in PBS) showed that SWB enhanced viral transduction in a concentration but not volume dependent manner.
Figure 12:
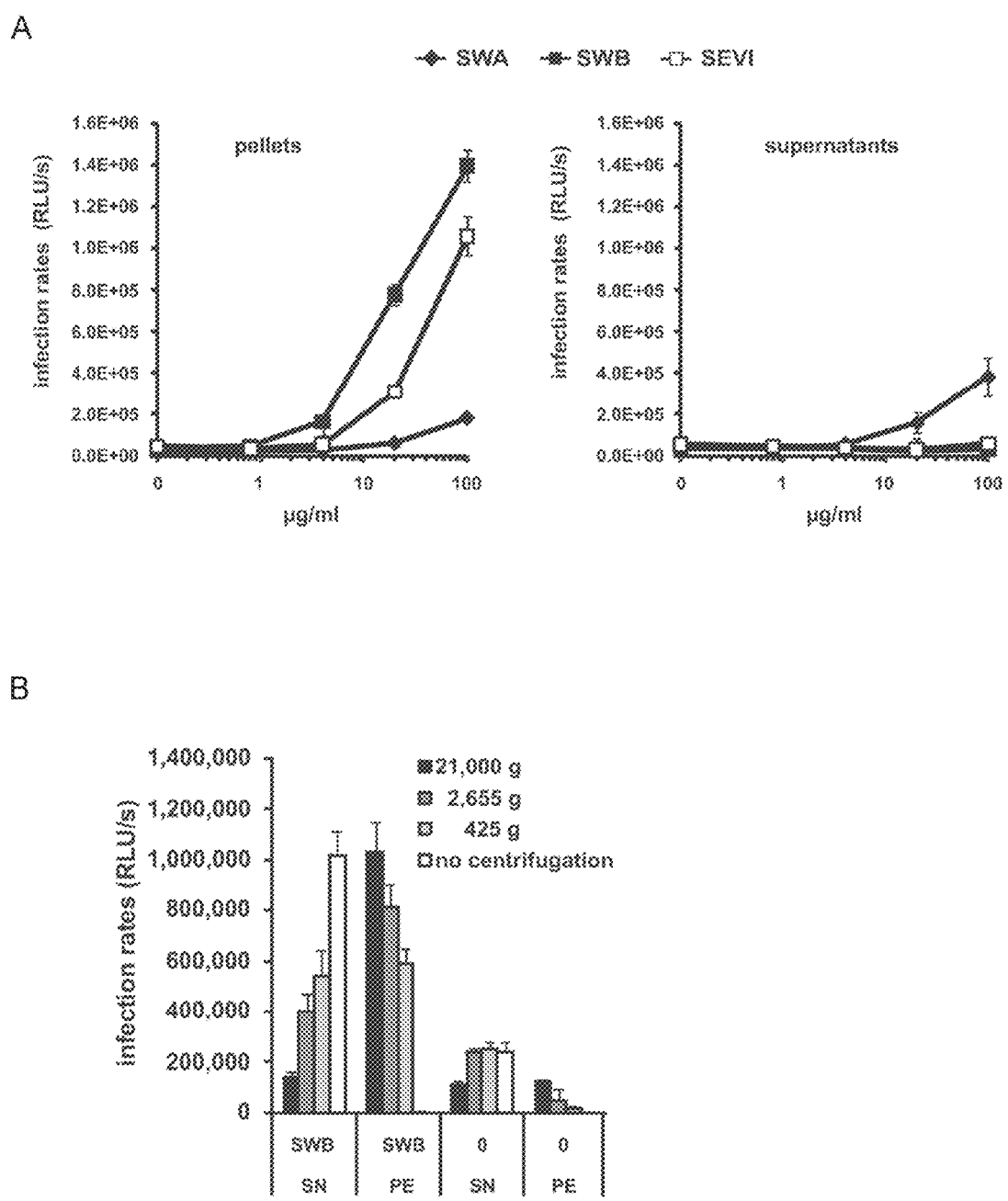
FIG. 12: The infectivity enhancing activity in SWB and SEVI solutions can be collected by centrifugation (A). Similarly, lentiviral particles were collected by mixing with SWB and subsequently centrifuging the mixture, wherein SWB and the lentiviral particles concentrated in the pellet (B—infection assay; C—p24 ELISA). Similar results were obtained using retroviral particles (D).
Figure 12:
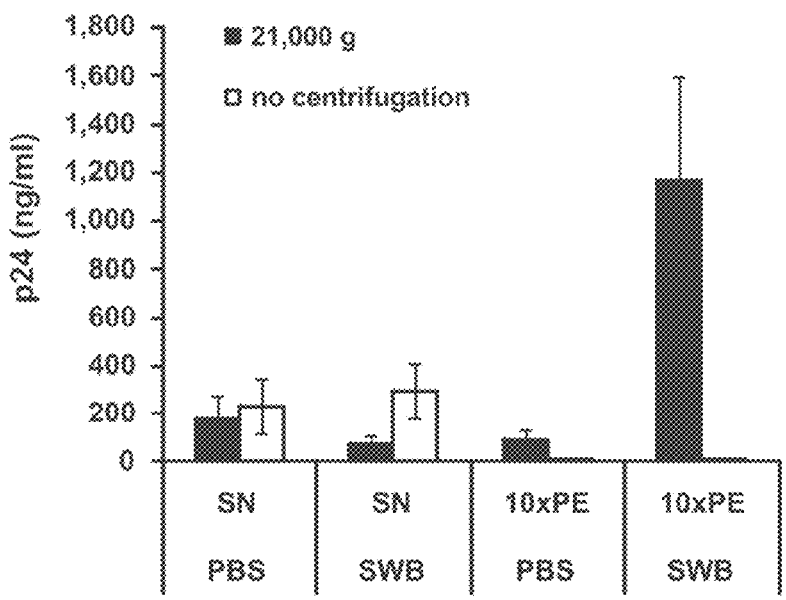
Figure 12:
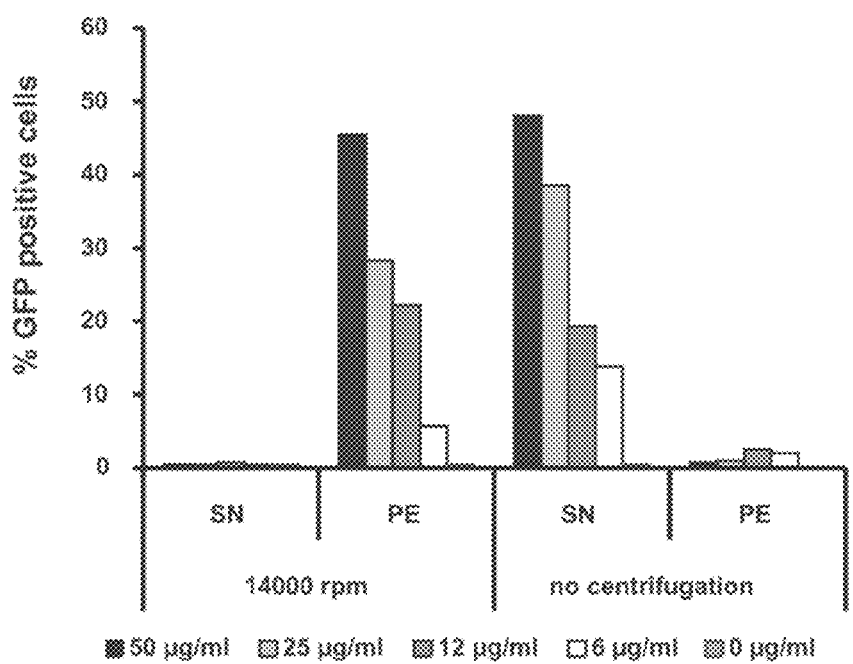

The terms "viral infection" and "infection" each refer to the introduction of a nucleic acid and/or other chemical components into a cell by means of a virus and/or a virus particle. They equally refer to self-replicable and non-self-replicable virus particles. Viral particles are also termed viral vectors when used for introducing a foreign gene into a cell (viral transduction). By infecting cells in the presence of insoluble aggregates of a viral infection enhancing peptide of gp120, i.e. a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 11 or SEQ ID NO: 12 the number of infected cells is increased compared to an infection of cells in the absence of the peptide (virus only control). Compared to SEVI, the peptides of the invention enhance viral infection more potently (FIG. 6 D, E, FIG. 12). In addition, they also lead to an earlier onset of the expression of genes introduced into the cell by the viral particle (FIG. 9 G-K).

In a preferred embodiment the cells are selected from the group consisting of mammalian cells, mammalian cell lines, mammalian primary cells, human 293T cells, HeLa cells, B/T cell hybrid CEM-M7, TZM-bl, K562 cells, Human Foreskin Fibroblasts (HFF) cells, murine NIH3T3 cells, hematopoietic progenitor cells, peripheral blood lymphocytes, stem cell-like cells, macrophages and CD34+ cells. The viral infection enhancing peptides are suited to enhance infection of most or all different types of cells (examples shown in FIGS. 6-9). Therefore, even cell types which are difficult to transduce, such as macrophages and stem cells, can be successfully infected in the presence of the peptide. In addition, since the peptide is suited for various types of cells it can be used to enhance viral infection in a broad range of different experiments even allowing serial infections of different cell types.

In a preferred embodiment the virus is selected from the group consisting of an enveloped virus, a retrovirus, a retroviral particle, a pseudotyped retroviral particle, a lentivirus, a lentiviral particle, a pseudotyped lentiviral particle, a VSV-G glycoprotein pseudotyped retro- and/or lentiviral particle, a GaLV glycoprotein pseudotyped retro- and/or lentiviral particle, a RD114 glycoprotein pseudotyped retro- and/or lentiviral particle, a MLV glycoprotein pseudotyped retro- and/or lentiviral particle and a spumavirus. The peptide of the invention enhances infectivity of many different types of viruses and virus particles (viral vectors) including pseudotyped viral particles (FIGS. 6-9). For biotechnical approaches viral particles which are used as viral vectors are often pseudotyped, which means they are carrying a specific foreign glycoprotein on their surface. The glycoprotein is selected according to the cell to be transfected, to optimize the interaction between the envelope's glycoproteins and the cell membrane, thereby optimizing viral infection. Since the peptide is suited to enhance infection by different viruses, it can be easily included in already established experiments. In addition, experiments can be designed and adjusted without any limitations due to the viral infection enhancing peptide.

In a preferred embodiment, introducing the peptide into the aqueous solution results in a peptide concentration of 4 to 100 µg/ml, preferably of 4 to 50 µg/ml, more preferred of 4 to 20 µg/ml. The peptide of the invention enhances viral infection at a concentration of as low as 4 µg/ml (FIG. 6 D). Due to the particular high efficiency of the peptide, only a small amount of peptide needs to be employed for each infection, optimizing the use of resources and further reducing costs.

In a preferred embodiment step c) of the in vitro method for enhancing viral infection of cells comprises applying the virus in a multiplicity of infection (MOI) of about 0.01 to about 0.5, wherein MOI is defined as infection events per cell in the absence of the peptide. In the presence of viral infection enhancing peptide the MOI is increased to about 0.1 to 5, improving the efficiency of the viral infection. Thus, the amount of virus applied to a given number of cells can be significantly reduced. Since the preparation of virus is particularly time and cost intensive the application of the peptide reduces the overall costs and time for performing viral infections.

In a preferred embodiment step c) of the in vitro method for enhancing viral infection of cells comprises
$c_1$) combining the solution with the virus, and
$c_2$) adding both to the cells.

Figure 11:
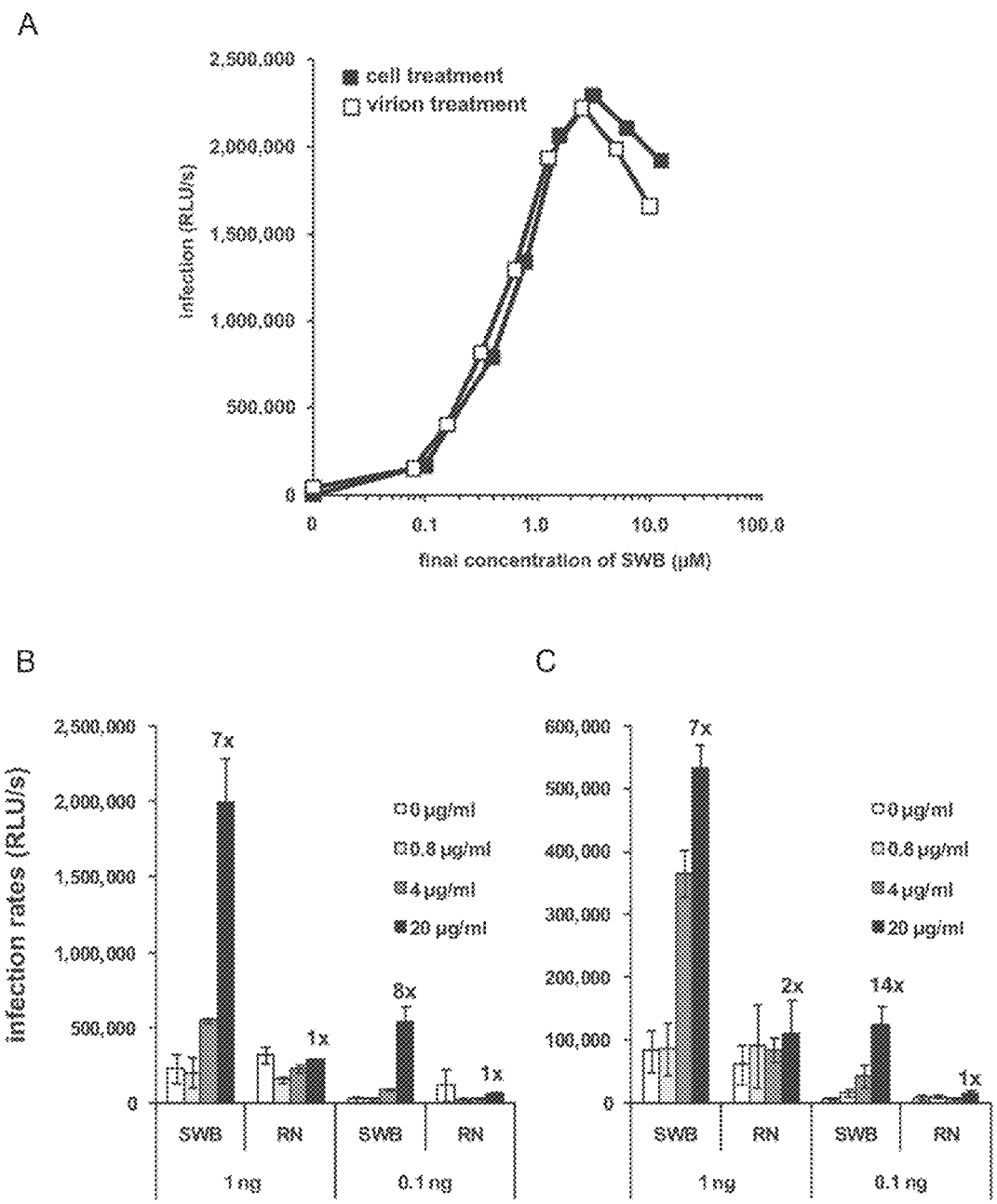
FIG. 11: SWB enhanced infection of TZM-bl cells when applied to the cells as well as to the virus (R5 HIV) (A). In contrast to RetroNectin® recombinant human fibronectin fragment, SWB supported infection of TZM-bl cells by R5 HIV-1 when applied to the virus (B) or to the cells (C) prior to infection.

In contrast to RetroNectin® recombinant human fibronectin fragment, the viral infection enhancing peptide of gp120 does not have to be coated onto a culture dish for enhancing infection. In contrast, it can be combined with the virus prior to infection (FIG. 11 A) and stored together with the virus if necessary. This further reduces the steps of a viral infection procedure, thereby decreasing the risk of contamination and the time required for accomplishing viral infections.

In a preferred embodiment step c) of the in vitro method for enhancing viral infection of cells comprises
$c_1$) combining the solution with the cells in a suspension, and
$c_2$) adding the virus to the suspension.

Since the peptide enhances infection of cells in suspension (FIG. 11), this allows an efficient viral infection of e.g. stem cells or stem cell-like cells such as neurospheres, which can only be infected in suspension since they immediately differentiate upon plating.

In a further aspect, the invention relates to an in vitro method for concentrating a virus comprising the steps of
a) providing a viral infection enhancing peptide of gp120 dissolved in an organic solvent,
b) introducing the peptide into an aqueous solution to obtain a solution comprising insoluble aggregates of the peptide,
c) adding the solution to a fluid comprising the virus,
d) centrifuging the fluid at about 2000 to 25000g, and
e) collecting a pellet,
wherein the virus is concentrated in the pellet.

When mixing the fluid comprising the virus with the insoluble aggregates of the peptide, the virus particles bind to the aggregates. Upon centrifugation, the virus particle deposits in the pellet together with the aggregates. Optionally, cells or cell debris may be removed from the fluid by filtration prior to adding the peptide. This method allows for separating a virus from a fluid without the need of conventional virus purification protocols including the use of ultracentrifuges (FIG. 12 B). Therefore, this method is easier to be carried out, less expensive and safer compared to standard methods.

In a preferred embodiment, the method further comprises the step
$f_1$) resuspending the pellet in fresh media and adding both to cells to be infected by the virus.

Retroviral and lentiviral particles are usually produced by the use of specific packaging systems comprising cell lines which produce all necessary proteins to produce viral particles. Conventionally, the virus has to be separated from the cell lysate and afterwards purified from the media by ultracentrifugation. In contrast, when adding the viral infection enhancing peptide, the virus can be collected by normal centrifugation (2000 to 25000 g) wherein the media is removed after centrifugation by discarding the supernatant. The remaining pellet can be resuspended in a media suited for culturing the cells to be infected. After collection, the virus is already combined with the viral infection enhancing peptide and may be immediately applied to infect cells without the need of any further purification or concentration steps.

In a preferred embodiment, the method further comprises the step
$f_2$) analyzing the virus concentrated in the pellet with respect to the amount of virus contained in the fluid, the identity of the virus, the genetic information of the virus and/or the infectivity of the virus.

The method for concentrating a virus may be combined with any analytical examination of the virus. It thus presents a fast and cost-effective method to collect virus for further analyzing the virus. For example it is possible to examine the purity of a virus sample or to identify the virus contained in a blood or urine sample. After concentrating the virus, it may also be added to cultured cells for investigating its infectivity or for further propagation.

In a preferred embodiment the fluid is selected from the group consisting of a cell suspension, a supernatant of a cell culture, preferably of a cell culture for a virus preparation and an isolated body fluid, preferably blood, serum or urine. Apart from concentrating virus from a virus preparation, the method can be applied to isolate viral particles from body fluids preferably for subsequently identifying and analyzing the virus. Thus, the method may be combined with conventional diagnostic tools for examination of viral infections.

In a further aspect, the invention relates to the use of a peptide comprising a sequence selected form the group consisting of SEQ ID NO: 1, 2, 3, 4, 5, 6, 7, 11 and 12 for enhancing infection of a cell with a virus in vitro.

In a preferred embodiment the peptide is in its aggregated form.

In a preferred embodiment the peptide is added to the virus prior to applying the virus to the cell.

In a preferred embodiment the cell is infected in suspension.

In a particularly preferred embodiment a further enhancer of viral infectivity, preferably recombinant human fibronectin fragment CH-2961, is applied. In specific applications, in particular for transduction of stem cells and for gene therapeutic applications, extremely high transduction rates are needed. By combining the peptide with a further viral infection enhancing agent, e.g. with recombinant human fibronectin fragment CH-2961 (i.e. RetroNectin®) transduction efficiency can be optimized (FIG. 14).

In a preferred embodiment the peptide is coated to a carrier prior to plating the cells onto the carrier. The peptide can be coated onto cell culture carriers, such as cell culture dishes or cover slips to enhance infection of cells. Since the viral infection enhancing peptide supports infection when plated as well as in suspension, the culture conditions may be chosen solely according to the requirements of the cells to be infected.

In a further aspect the invention relates to the use of a peptide comprising a sequence selected of the group consisting of SEQ ID NO: 1, 2, 3, 4, 5, 6, 7, 11 and 12 for binding a virus to a carrier by coating the carrier with the peptide. When applied to a carrier coated with the peptide, the virus binds to the peptide and becomes thereby attached to the carrier. Upon binding of the virus, the remaining fluid can be removed and replaced by fresh media comprising the cells to be infected. Alternatively, upon removing the fluid, a fresh solvent may be added and the peptide removed from the carrier such that peptide and virus can be collected for further applications.

A further aspect of the invention relates to the use of a peptide comprising a sequence selected of the group consisting of SEQ ID NO: 1, 2, 3, 4, 5, 6, 7, 11 and 12 for isolating a virus from a fluid, preferably from a human body fluid.

A further aspect of the invention relates to the use of a peptide comprising a sequence selected of the group consisting of SEQ ID NO: 1, 2, 3, 4, 5, 6, 7, 11 and 12 for concentrating a virus from a fluid preferably from a human body fluid.

EXAMPLES

Material and Methods

HIV-1 was produced from pBRHIV-1NL4-3 92Th014, a plasmid containing a CCR5 tropic molecular HIV-1 clone (Papkalla, et al., 2002). Infectious HIV-1 stocks were prepared by transfection of 293T cells by calcium phosphate transfection and viral titers were determined by p24 Elisa (AIDS reagent and reference programme, SAIC Frederick, USA).

Retroviral vectors were produced using pSRS11 SF GFP-pre and M57-DAW and pseudotyped with glycoproteins derived from Gibbon ape Leukemia Virus (GaLV) and Vesicular Stomatitis Virus (VSV-G). Luciferase expressing retroviral vectors were generated by cotransfecting a luciferase encoding Mouse leukaemia virus vector with M57-DAW and various glycoproteins derived from Gibbon Ape Leukemia Virus (GaLV), endogenous feline leukemia virus (RD114), Vesicular Stomatitis Virus (VSV-G) or Murine leukemia virus (MLV).

Lentiviral vectors were produced by transient transfection of 293T cells with pRRL.cPPT.SFeGFP.pre, pRSV-Rev, pMDLg/pRRE and phCMV-RD/TR or phCMV-GaLV/TR encoding chimeric envelope glycoproteins (gp) derived from Feline Leukemia Virus or Gibbon ape Leukemia Virus with the cytoplasmic tail derived from the MLV gp. Luciferase encoding lentiviral particles were generated by cotransfection of an env deleted pBRHIV-1 NL4_3 derivative encoding luciferase instead of nef and various glycoproteins derived from Gibbon Ape Leukemia Virus (phCMV-GaLV/TR), endogenous feline leukemia virus (phCMV-RD/TR), Vesicular Stomatitis Virus (VSV-G) or amphotropic Murine leukemia virus (phCMVA).

Peptides were synthesized using a solid-phase peptide synthesis (SPPS) method on acid-labile resin. The peptide elongation was carried out by using a Fmoc protection scheme, and the completion of the amino acid coupling reaction was determined by the anhydrin test. Crude peptides were purified by conventional High Performance Liquid Chromatography (HPLC) method and a gradient of acetonitrile in aqueous buffer solutions. The purified peptides were dried by lyophilization and characterized by analytical HPLC and mass spec analysis. Peptides were dissolved in DMSO to 10 mM or 10 mg/ml stocks and stored at −20° C.

Results

Identification of a HIV-1 gp120 Derived Peptide Enhancing Virus Infection

The inventors surprisingly found that the synthetic peptide SW1010 (FIG. 1 A) corresponding to the beta 19 and beta 20 strands in the glycoprotein gp120 of the HIV-1 MN strain (Gurgo et al., 1988), forms a turbid solution reminiscent of SEVI, an amyloid-containing turbid-white solution. When analyzing the effect of SW1010, the inventors further found that in the presence of 12.5 μg/ml SW1010, infection rates of the CXCR4 (X4) tropic HIV-1 strain NL4-3 in the reporter cell line TZM-bl were increased by 17 fold, and that of the CCR5 (R5) tropic variant 92TH014-2 by 34 fold, relative to control infections containing no peptide (0 μg/ml) (FIG. 1 B). Therefore, further peptides corresponding to the beta 19 and beta 20 strands in the glycoprotein gp120 of the HIV-1 (referred to as SW peptides henceforth) were generated: N- (SW1014) and C-terminal (SWA) halves of SW1010, variants with different length of the peptide (SWB, SWC, SWD, SWE and SWF), as well as two peptides that were derived from a SW1010 homologous consensus sequence of all HIV-1 M strains (SWCON) and from the molecular HIV-1 clone NL4-3 (SWNL43) (FIG. 1 A).

SW Derived Peptides have Amyloid Like Properties

To investigate if SW1010 (like PAP248-286) forms insoluble aggregates, in particular amyloid like material, the reactivity of a freshly prepared SW1010 peptide solution to the amyloid specific dye Thioflavin T (ThT) was analyzed. ThT is a benzothiazole dye that exhibits enhanced fluorescence upon binding to amyloid fibrils and is commonly used to diagnose amyloid fibrils. ThT fluorescence scans showed that a SW1010 solution that was freshly prepared by diluting the DMSO stock (10 mg/ml) tenfold in PBS (1 mg/ml) resulted in a strong ThT signal (FIG. 1 D, 2 A). Further evidence that SW1010 forms amyloid like material was derived by staining with another amyloid specific dye, Congo Red (CR) (Münch et al., 2007). In contrast to the PBS control, the SW1010/CR solution formed a red colored pellet after centrifugation, indicating that the dye specifically intercalated into SW1010 aggregates (FIG. 1 E, 2 B). However, electron microscopy studies did not reveal the presence of classical amyloid fibrils in a SW1010 solution suggesting that the freshly diluted peptide displays some amyloid like properties (ThT and CR staining) but cannot be classified as amyloid per definition, since it does not form amyloid fibrils (FIG. 1 C). These data are in agreement with the very rapid generation of virus enhancing material that occurred immediately after diluting the clear DMSO stock in PBS, whereas amyloid fibrils typically take several hours or days to form. Thus, when used to enhance retroviral infection or transduction efficiencies (FIG. 1 F), the peptide of the invention provides an important advantage over SEVI amyloid fibrils that have to be generated by agitating the monomeric PAP248-286 by several hours or days on a table rotator (Münch et al., 2007; Wurm et al., 2009).

Similarly, all SW1010 derivatives were analyzed for ThT and CR reactivity. ThT fluorescence excitation spectra showed that solutions containing the peptides SW1014, SWB, SW1010, SWE and SWCON displayed increases fluorescence intensities indicating the presence of structures with amyloid like properties (FIG. 2 A). In agreement with these data the CR staining assay showed specific staining of solutions containing SW1010, SW1014, SWB, SWE and SWCON but also of SWC whereas SWA, SWD, SWF and SWNL43 did react with CR to a lesser extend (FIG. 2D).

Several SW1010 Derivatives Enhance HIV Infection

To determine the effect on HIV-1 infection, stocks of the CCR5 tropic HIV-1 NL4-3 92TH014-2 variant (R5 HIV-1) were generated by transient transduction of 293T cells with proviral DNA, and harvested 2 days later. The viral titer was determined by p24 Enzyme Linked Immunosorbent Assay (ELISA) and virus dilutions containing 1, 0.1 and 0.01 ng p24 antigen were treated with various concentrations of freshly prepared SW peptides. Infection experiments performed in TZM-bl cells showed that most SW peptides led to increased reporter gene activities (FIGS. 6 A-6 C). For example, treatment of 1 ng virus with 100 μg/ml of SW1010, SWA, SWB, SWC, SWE and SWCON enhanced HIV infection between 9 to 12 fold, whereas SW1014, SWD, SWF and SWNL43 displayed weak or no effects (FIG. 6 A). At the lowest viral dose used (0.01 ng), the most potent enhancers of HIV infection were SW1010, SWB, SWC, SWE and SWCON (FIG. 6 C). The HIV enhancing activity partially correlated with the reactivity to CongoRed and thus with the formation of amyloid like material upon dilution in PBS. These data show that the central region of SW1010 (FIG. 1 A) is sufficient to form insoluble aggregates enhancing HIV-1 entry into target cells. From all tested SW peptides, SWB promotes HIV-1 infection most potently.

SW Peptides are not Cytotoxic and Cell Agglutinating

Figure 4:
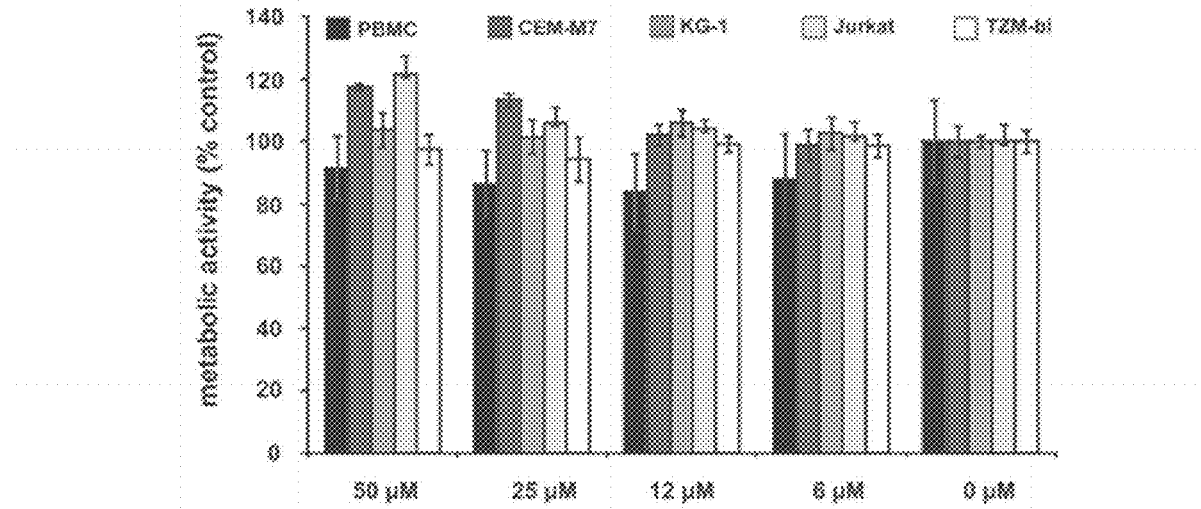
FIG. 4: Insoluble aggregates of SWB did not impair the metabolic activity of various cell lines (A). Metabolic activity of TZM-bl cells was not impaired by viral infection enhancing peptides of gp120 (B). Koeffler Golde-1 (KG1) cells were incubated with indicated concentrations of SWB and fluorescence activated cell sorting (FACS) analyzed after indicated time points showing that SWB did not exhibit autofluorescence in the GFP channel (C). The percentage of cells associated in cell clusters were microscopically analyzed using a Neubauer counting chamber (D). FACS analyses in the absence of cells of PBS only, SWB only, a lentiviral vector (LV) preparation only ("virus only"), and a mixture of SWB/virus (E), depicting the aggregates formed by SWB and virus particles.
Figure 4:
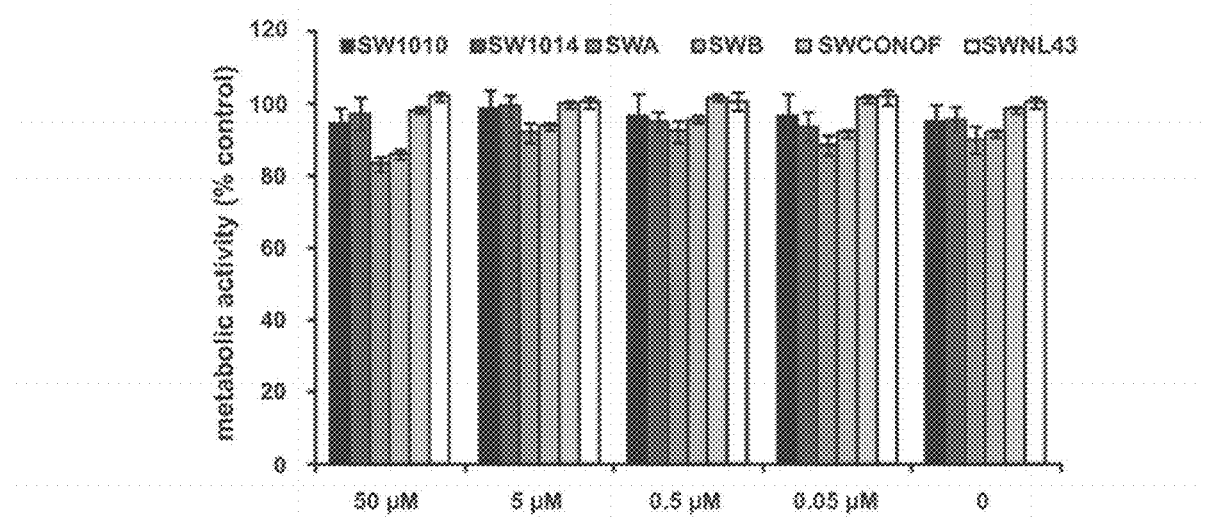
Figure 4:
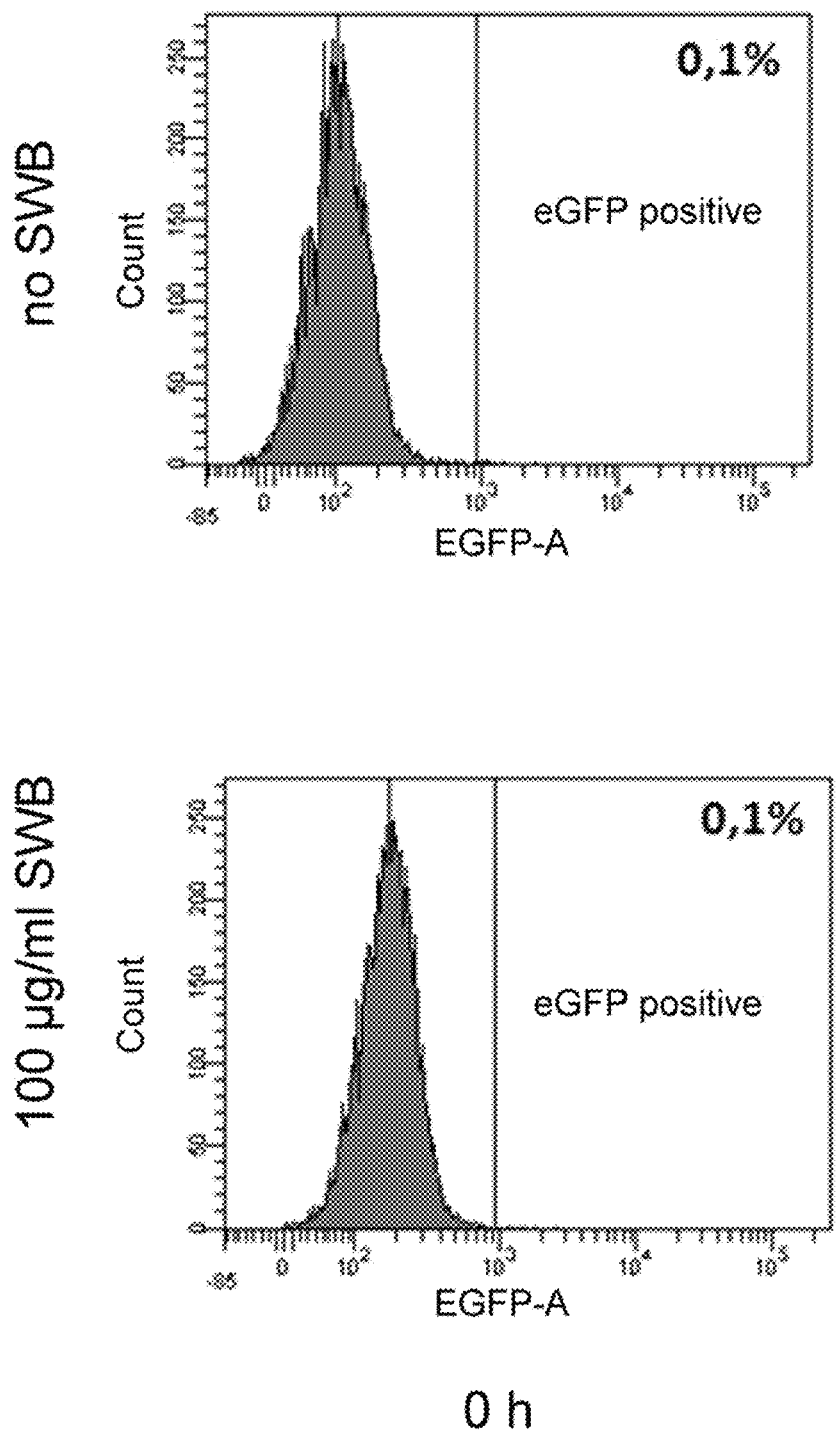
Figure 4:
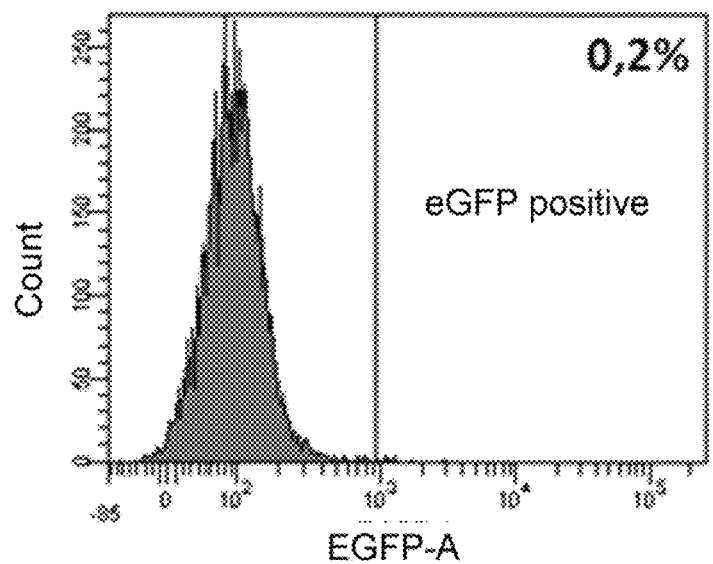
Figure 4:
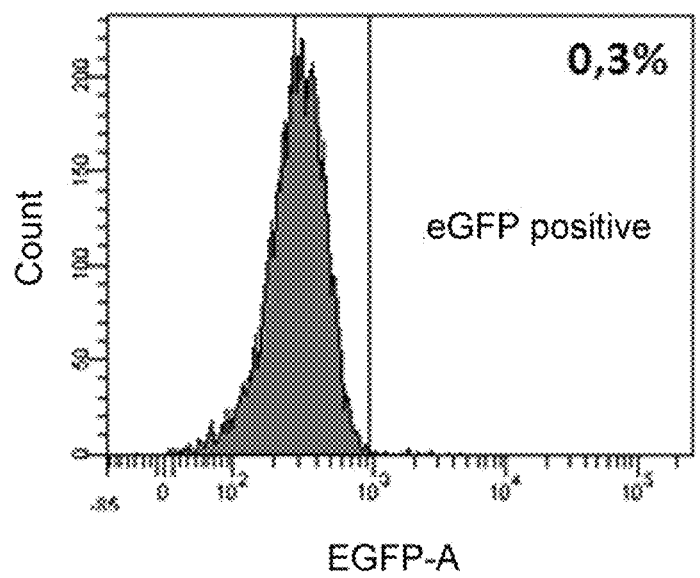
Figure 4:
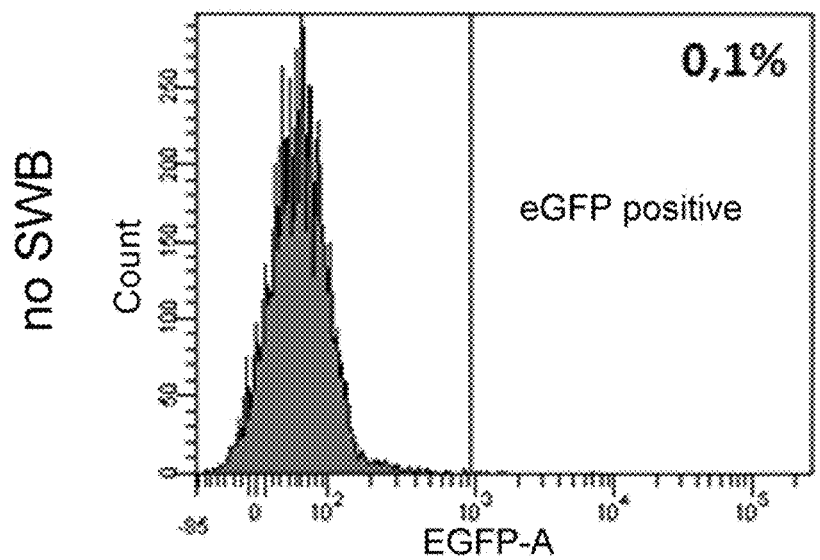
Figure 4:
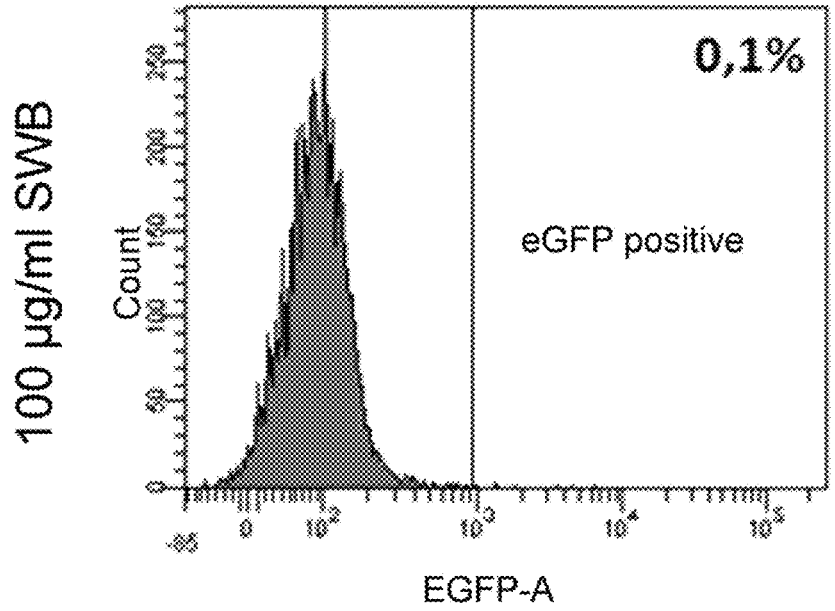
Figure 4:
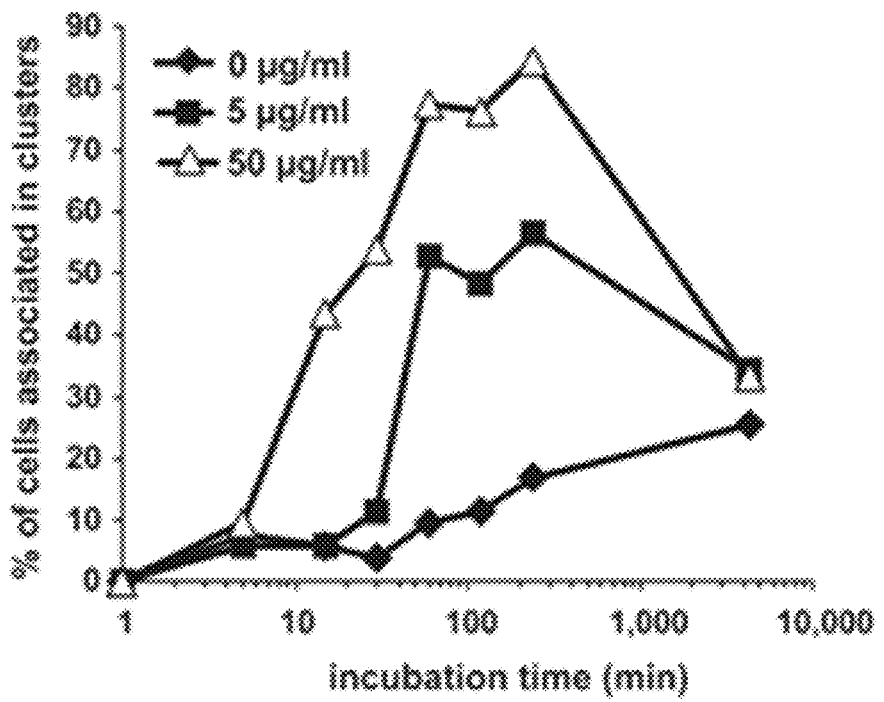
Figure 4:
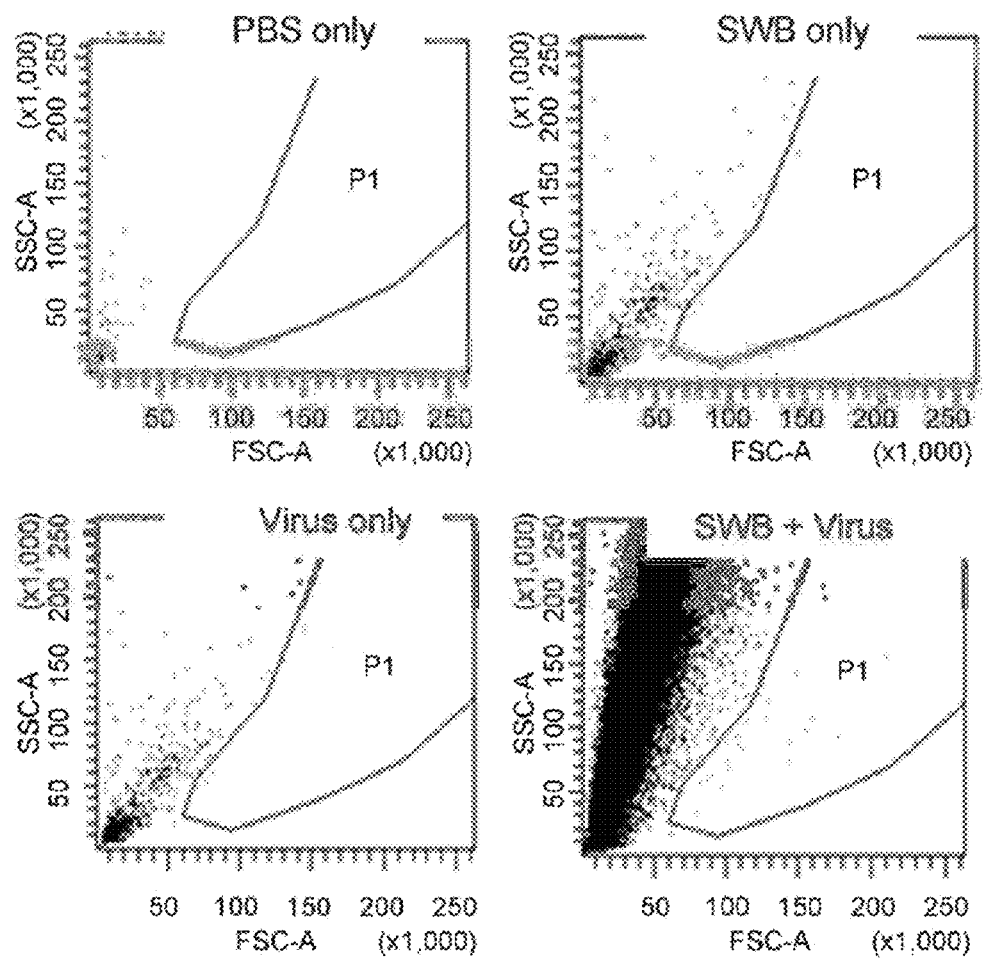

To analyze possible cytotoxic effects, freshly dissolved SW peptides were incubated with TZM-bl cells for three days, and then the metabolic activity in these samples was assessed by quantification of intracellular ATP levels showing that none of the peptides affected cell growth (FIG. 4 A). Further analysis of the most potent HIV enhancing peptide, SWB (see following paragraphs), showed no toxic effects for primary peripheral blood mononuclear cells (PBMC), for CEM-M7 cells, a B/T cell hybrid cell line, for KG-1 cells, a progenitor like cell line and for Jurkat T cells (FIG. 4 B).

Additionally, FACS analyses of the stem cell like cell line KG-1 incubated with SWB demonstrated that SWB amyloid did not exhibit auto-fluorescence in the GFP channel demonstrating that it does not interfere with standard FACS measurements. Further analyses revealed a transient increase of cell clusters containing SWB peaking at 4 hrs but declining to base line levels 3 days post infection (FIG. 4 C, D). In agreement with the interaction of SWB with cellular membranes, FACS analyses of SWB treated virus resulted in a strong signal, compared to the signals obtained from SWB or virus only containing samples (FIG. 4 F). In sum, these data are evidence that SWB and related peptides are not cytotoxic. Furthermore they propose that the underlying mechanism in enhancing virion infectivity is mediated by interaction of SWB with the cellular and viral membranes increasing attachment and hence infection/transduction rates.

SWB is the Most Potent Enhancer

To identify the peptide with the most potent HIV enhancing activity the inventors performed additional assays and compared the effect of several SW1010 derivatives on HIV-1 infection. It turned out, that the peptide SWB reproducibly increased HIV-1 infection rates most efficiently (FIG. 6 A-C). Using ThT and Chromium Release (CR) assays they also found that the amounts of amyloid like material in SWB solutions were increased compared to those in SW1010 stocks, suggesting that amyloid like material in SWB is responsible for infectivity enhancement (FIG. 2 A, B).

Dilution of SWB in DMSO

To test if SWB is soluble in solvents other than DMSO and can form virus enhancing amyloid like material upon diluting in PBS, the inventors resuspended SWB powder in various solvents. CR assays performed with 10 fold dilutions of these stock solutions in PBS revealed that the DMSO stock solution contained the highest reactivity to CR, followed by acetic acid and guanidinehydrochloride stocks (FIG. 5 A), whereas the polar solvents PBS and $H_2O$/water contained no or only subtle amounts of CR stainable material. In agreement with these data, DMSO and acetic acid stocks enhanced HIV infection most efficiently whereas SWB reconstituted in PBS, $H_2O$ or PBS was largely inactive (FIG. 5 B). Since acetic acid stocks were highly toxic for cell culture at higher concentrations, all following SWB stock solutions were then prepared by dissolving the peptide in less cytotoxic DMSO. In all subsequent experiments the concentrations of DMSO in the presence of virus or cells were lower than 1%, preferably between about 0.2 and about 1%.

Since trace amounts of DMSO might nevertheless interfere with biological assays, the inventors tried to further decrease the final concentration of DMSO in the active amyloid like material containing solutions. To this end, first the solubility limit of SWB in DMSO was determined and it was found that concentrations above 25 mM (38 mg/ml) were not completely dissolved. Next, formation of amyloid like material was induced by diluting the 10 and 25 mM SWB stock solutions in PBS resulting in 200 μM solutions containing 2% or 0.8% DMSO, respectively. After generating additional dilutions in PBS, 40 μl of these SWB dilutions were incubated with 40 μl R5 HIV-1 yielding 1 and 0.4% DMSO at the highest concentration of SWB (i.e. 100 μM). Thereafter, TZM-bl cells were infected and β-galactosidase activities were detected 20 hrs later. These results showed that dilutions of both stock solutions of 10 mM and 25 mM resulted in the formation of amyloid like material with comparable HIV enhancing activities (FIG. 5 C).

The Virus Enhancing Activity of SWB Dilutions is Stable Over Time

Formation of amyloid like material was induced by diluting a 10 mM SWB DMSO stock in PBS down to a 200 μM solution that was then stored at 4 or -20° C. After 2 weeks, both samples and a freshly prepared SWB solution were further diluted and analyzed for their HIV enhancing activity. Infection assays revealed that the stored peptide solutions increased virus infection with almost the same activity as the freshly prepared peptide (FIG. 5 D). Thus, SWB amyloid can be stored without significant loss of activity for prolonged periods of time.

SWB is a More Potent Enhancer than SEVI

It has been shown that in the presence of SEVI fibrils just 1-3 virions are sufficient to yield a productive HIV-1 infection (Münch et al., 2007) and that SEVI is a useful tool to boost retroviral gene transduction. Compared to SEVI, SWB has a markedly reduced size (12 amino acid residues) and forms insoluble aggregates immediately upon dilution in PBS. To directly compare the HIV enhancing activity of SEVI and SWB, 0.1 ng R5 HIV-1 virions (FIGS. 6 D) and 0.01 ng R5 HIV-1 virions (FIG. 6 E) were treated with equal concentrations of freshly prepared SWB or preformed SEVI fibrils. After 5 min incubation, these mixtures were used to infect TZM-bl cells. Infection rates determined 2 days later showed that SWB treated virus was more infectious than HIV treated with equal concentrations of SEVI (FIG. 6 D, E). Thus, SWB has three major advantages over SEVI; i) it is smaller in size and easier to synthesize thus reducing the costs; ii) SWB forms amyloid like material immediately after mixing it with PBS, which means within the first 10 seconds, mostly within the first 0.5 to 3 seconds after mixing with PBS, whereas SEVI has to be generated by agitating over night; iii) SWB enhances virus infection more potently.

Formation of Insoluble Aggregates by SWB can be Achieved in Several Solvents

Figure 3:
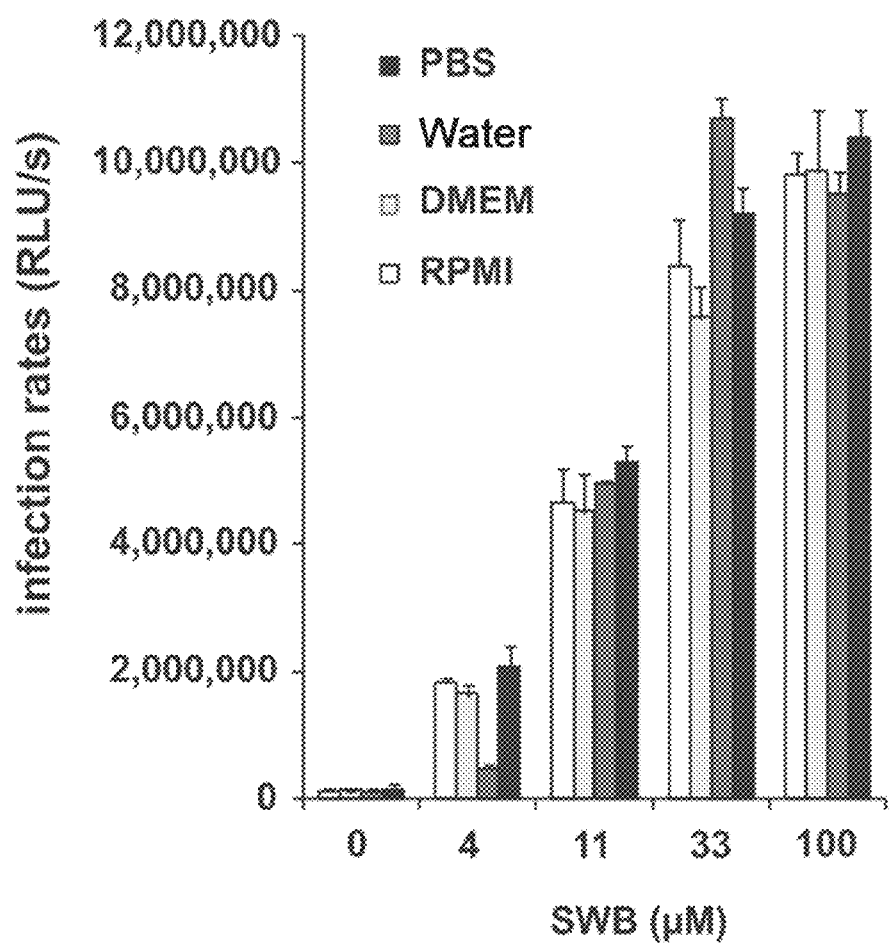
FIG. 3: SWB insoluble aggregates, induced by different aqueous solutions, enhanced viral infection similarly.

For certain experimental setups it might be beneficial to dilute SWB stocks (10 mM in DMSO) in other buffers than PBS to form virus infectivity enhancing material. To test this, the inventors diluted a 10 mM SWB stock in DMSO 50-fold in either PBS, $H_2O$/water or cell culture media RPMI 1640 (Gibco) or DMEM (Gibco). The resulting 200 μM solutions were further diluted 3-fold and mixed with R5 HIV-1. TZM-bl cells were inoculated and infection rates determined by luciferase assay 2 days later. All tested solvents including the two cell culture media resulted in SWB preparations with similar HIV enhancing activity (FIG. 3). Thus, amyloid like material can be formed in solvents that might be advantageous for several approaches e.g. in experiments with cells depending on specific media.

SWB Enhances Transduction of Various Cell Types

Figure 7:
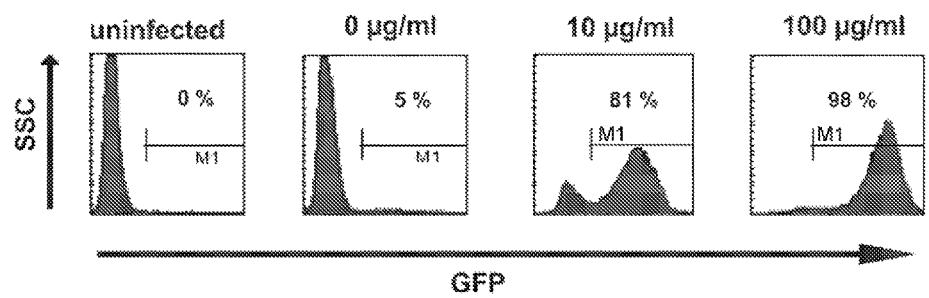
FIG. 7: SWB enhanced infection of HeLa cells (A) and of HFF cells (B-D) by gibbon ape leukemia virus (GaLV) gp retroviral particles comprising enhanced Green Fluorescent Protein (eGFP).
Figure 7:
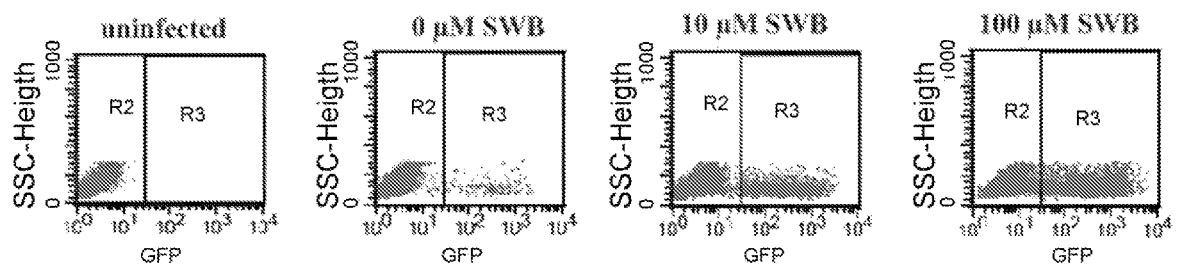
Figure 7:
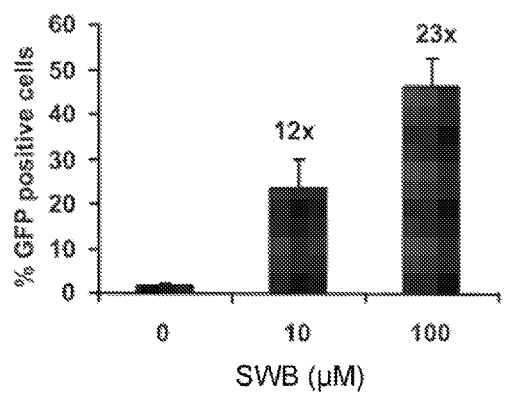
Figure 7:
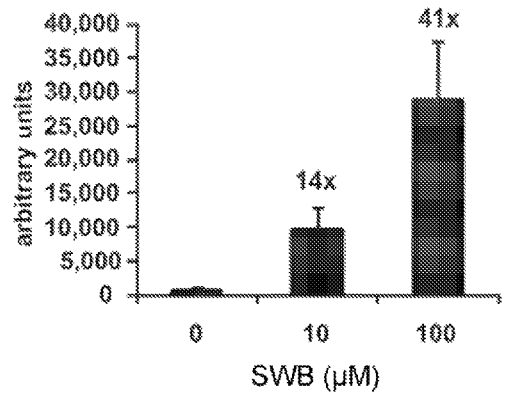

To analyze whether the transduction enhancing effect of SWB might be restricted to certain cell types, the inventors investigated its influence on the efficiency of retrovirus (RV) or lentivirus (LV) mediated gene transfer in various cell lines and primary cells. It was found that SWB treatment of a GFP expressing RV vector carrying the GaLV gp increased transduction of adherent HeLa cells from 5% in the control to 98% after 100 μg/ml SWB treatment (FIG. 7 A). Since it has been reported that adherent HFF cells are relatively refractory to retroviral transduction it was tested whether SWB enhances gene transfer into these cells as well. A treatment of RV/GaLV particles with SWB resulted in 46% GFP positive cells 3 days post transduction whereas only 2% were transduced in the absence of the enhancer (FIG. 7 B), corresponding to a 23-fold enhancement of transduction rates (FIG. 7 C). Calculating the arbitrary units revealed an even better enhancement suggesting that SWB does not only increase the percentage of infected cells but also the transduction rate per single cell (FIG. 7 D).

Figure 8:
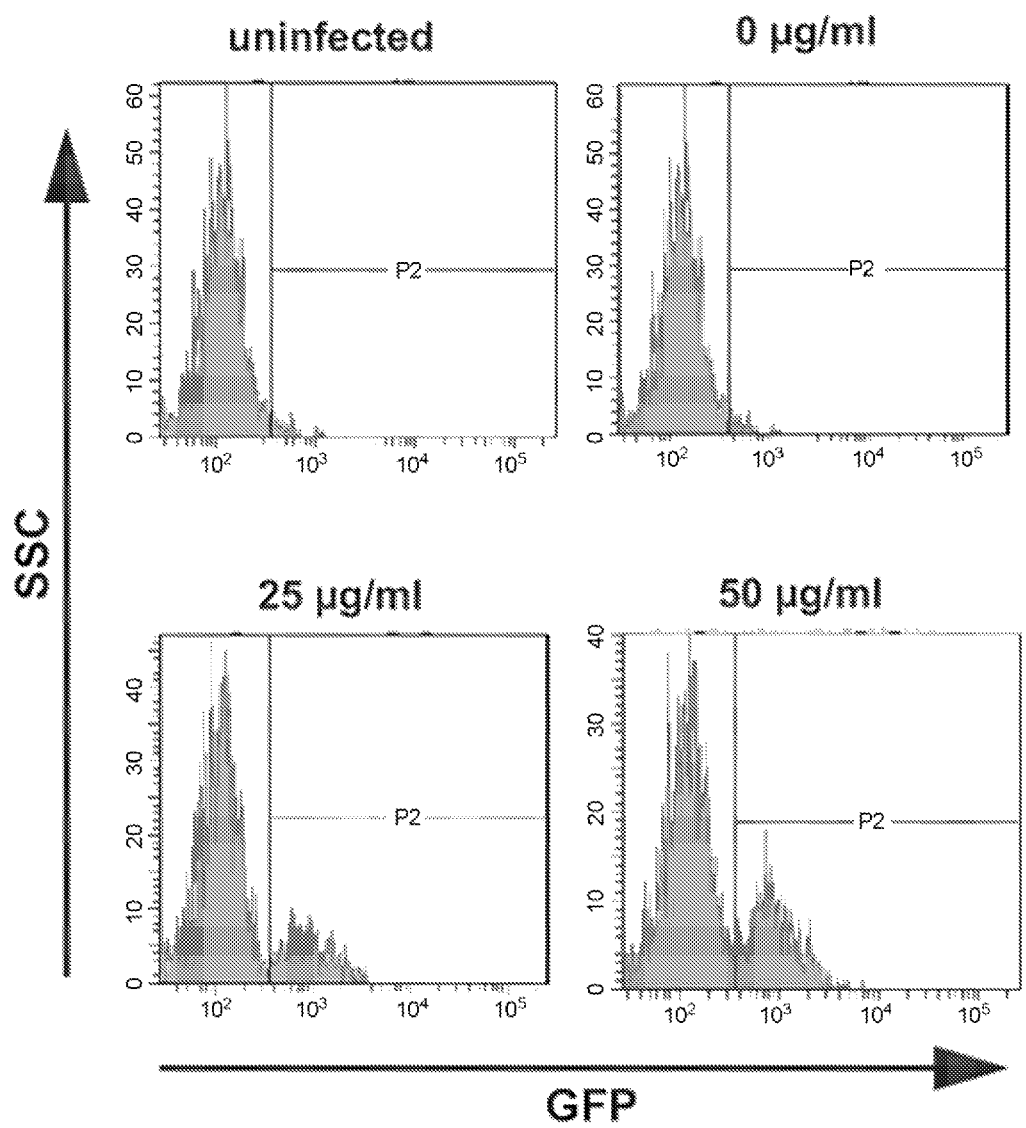
FIG. 8: SWB enhanced infection of human CD34+ cells (A, B) and peripheral blood lymphocytes (D) by RD144 gp lentiviral vectors comprising eGFP. SWB enhanced infection of KG-1 cells by GaLV gp retroviral vectors comprising eGFP (C) and of macrophages by RD144 gp lentiviral vectors comprising eGFP (E).
Figure 8:
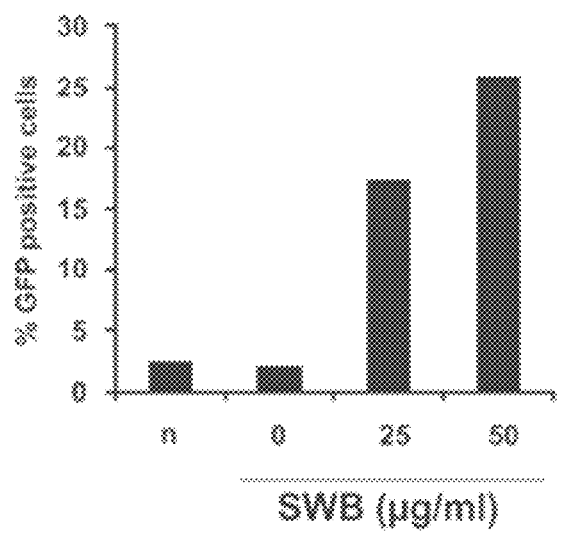
Figure 8:
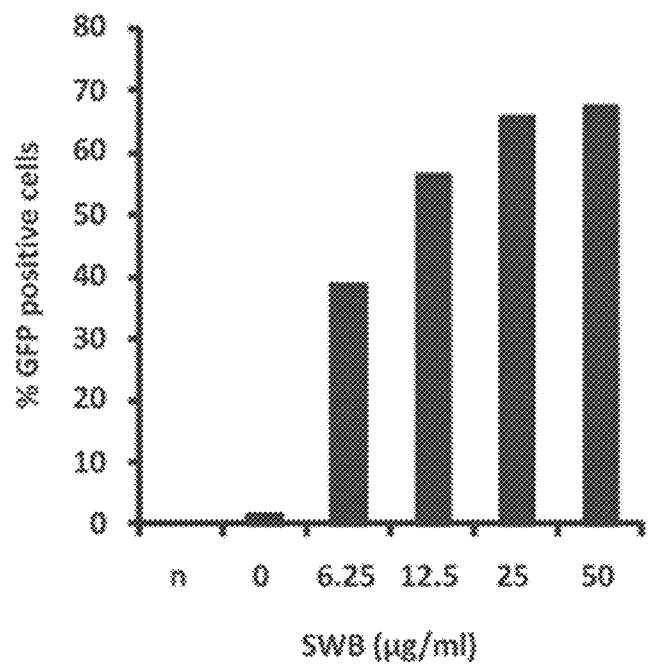
Figure 8:
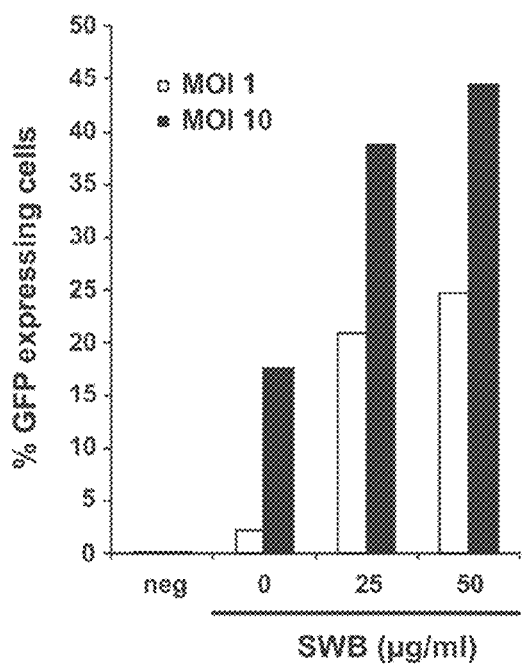
Figure 8:
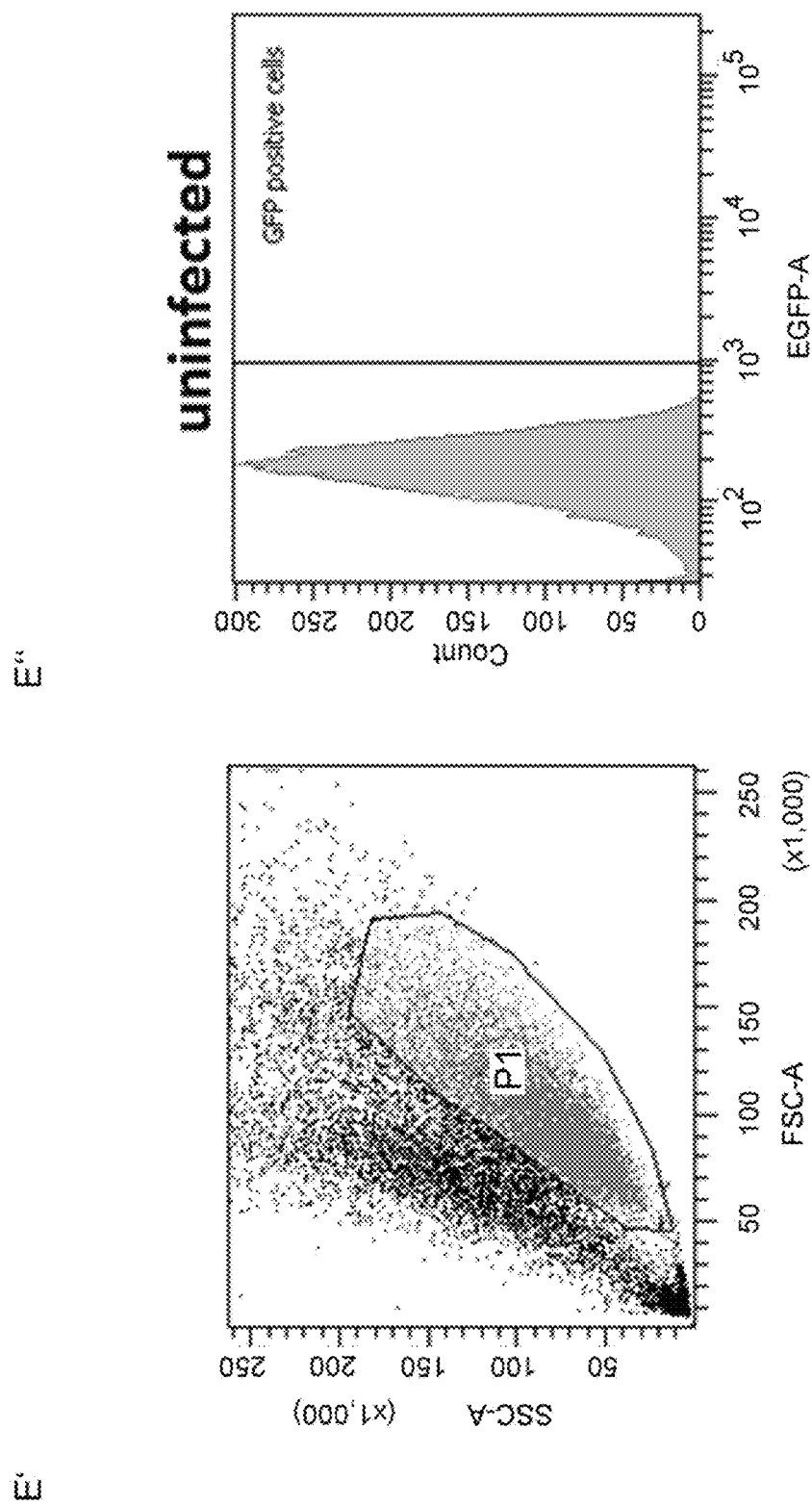
Figure 8:
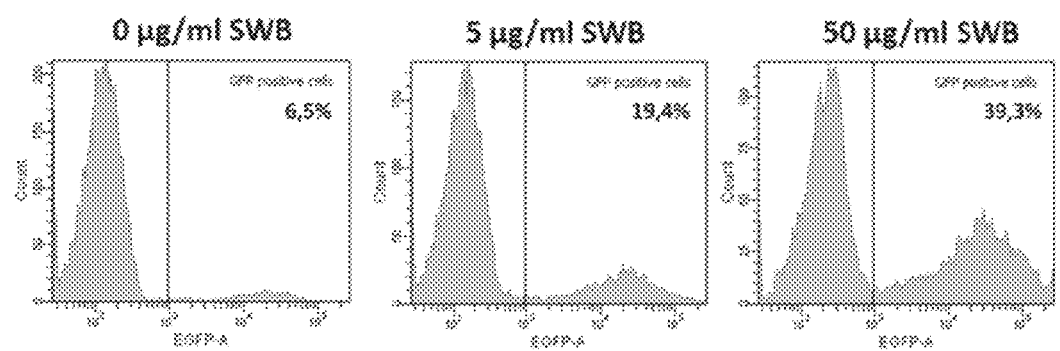

Genetic modification of stem cells and their transplantation is a widely used method in biology and will also play an important role in the therapy of a variety of diseases. To test whether SWB enhances transduction of stem cells, human hematopoietic stem cells (HSC) were incubated with an RD114 pseudotyped lentiviral vector that has been treated with SWB or PBS prior to infection. FACS analyses performed 4 days after inoculation showed that transduction of SWB treated vector resulted in more than 25% of transduced and GFP positive cells, whereas inoculation with untreated virus showed transduction rates of 5% only (FIG. 8 A). These results demonstrate that SWB treatment of a vector preparation markedly enhanced gene transfer into HSCs. Thus, SWB allows efficient transduction of stem cells even with limiting amounts or titres of viruses.

When analyzing the transduction efficiencies in KG-1 cells, a human acute myeloid leukemia cell line that represents an early stage of hematopoietic differentiation and that is often used in colony formation assays instead of human bone marrow cells, it was found, that these relatively transduction refractory cells can be efficiently transduced in the presence of SWB (FIG. 8 C). The rate of GFP expressing cells was 2% in the control whereas treatment with 50 μg/ml SWB led to GFP expression in almost 70% of the cells (FIG. 8 C).

To analyze the transduction enhancing activity of SWB in primary cells phytohemagglutnin/interleukin-2 (PHA/IL-2) activated Peripheral Blood Mononuclear Cell (PBMC) were transduced with a high and a median MOI (multiplicity of infection) of a LV vector containing the RD114 env in the presence or absence of SWB. FACS analyses revealed that SWB increased the percentage of GFP positive cells after infection with a MOI of 1 from 2.3% to more than 24% and after infection with a MOI of 10 to a maximum of 44% (FIG. 8 D). To test, whether SWB might also favor transduction of macrophages that are considered as hard to transduce cells, macrophages were inoculated with RD114 pseudotyped LV vector that were either treated with SWB or PBS. FACS analysis performed 5 days later demonstrated that 50 μg/ml SWB treated virus transduced more than 39% of the cell whereas only 6.5% expressed GFP after infection with untreated viral vector. (FIG. 8 E). In sum, these results show that SWB generally and efficiently enhances transduction of primary cells.

Experiments performed in non-adherent K562 cells, a human immortalized myelogenous leukaemia line, showed that both, retroviral (RV) and LV vectors either carrying VSV-G or GaLV gp, transduced cells more efficiently when treated with SWB (FIG. 9 B-D). Thus, SWB does not only favor transduction of adherent cells but also of those growing non-adherently. In addition SWB mediated enhancement of gene transfer in mouse cells was tested by infecting NIH3T3 cells with a RV vector pseudotyped with Murine leukemia virus Env (MLV) (FIG. 9 A). Again SWB enhanced the rate of GFP positive cells indicating that SWB favours transduction not only in human cells but also in mammalian cells in general.

SWB Increases Transduction Efficiency of LV or RV Vectors Pseudotyped with Various Glycoproteins The effect of SWB on transduction enhancement of 293T cells was analyzed for transduction by LV and RV vectors with different envelopes routinely used for genetic modification of the cell, including the Gibbon Ape Leukemia Virus env (GaLV gp), the endogenous feline leukemia virus env (RD114-gp), the Vesicular Stomatitis Virus spike protein (VSV-G) or Murine leukemia virus Env (MLV-gp) as well as variants thereof containing mutations in the cytoplasmic domain allowing incorporation into lentiviral particles (phCMV-RD/TR and phCMV-GaLV/TR). Therefore, indicated luciferase encoding RV (FIG. 9 E) and LV (FIG. 9 F) vectors pseudotyped with various glycoproteins were combined with SWB, and 293T target cells were infected with those mixtures. Luciferase assays performed 2 days after infection demonstrated that SWB concentrations between 5 to 100 μM (i.e. during virion treatment) enhanced transduction rates of all analyzed vectors, except for those carrying no glycoprotein (no env) indicating that SWB does not allow unspecific entry into target cells. Overall, luciferase activities in cellular lysates infected with untreated LV particles resulted in values below $5.0\times10^5$ RLU/s, whereas infection rates of 100 µM SWB treated virus were increased up to $6.5\times10^6$ (RD114-tr) or even $1.4\times10^7$ RLU/s (MLV) (FIG. 9 F). Similar results were obtained for RV particles (FIG. 9 E). With the exception of the VSV-G pseudotype ($1.6\times10^5$ RLU/s), reporter gene activities after infection with untreated vectors were below $3\times10^4$ RLU/s, but were markedly increased after infection with SWB treated virions (FIG. 9 E).

Figure 13:
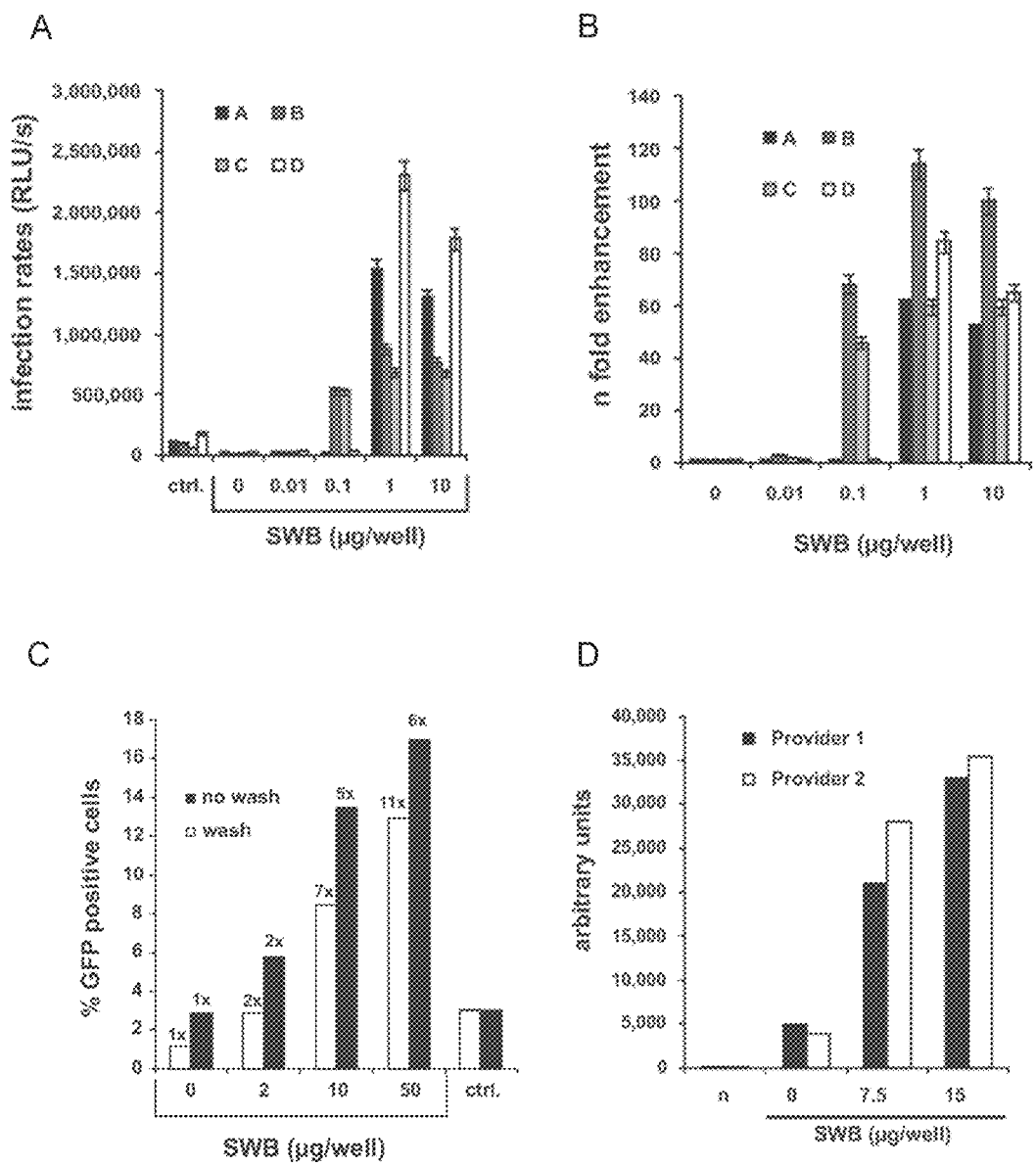
FIG. 13: SWB coated on microtiter plates enhanced infection of TZM-bl cells by R5 HIV independently of the provider of the microtiter plates (A, B). R5 HIV infection rates of CEM-M7 cells were increased in SWB treated microtiter plates regardless of whether the cells were added immediately after removing the virus inoculum (no wash) or after an additional washing step (wash) (C). Regardless of the source of microtiter plates the increased infection of HeLa cells by VSV-G retroviral vector expressing eGFP was increased if the microtiter plates were coated with SWB over night (D).
Figure 14:
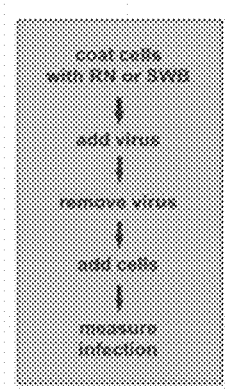
FIG. 14: When coated onto microtiter wells, both SWB and RetroNectin® recombinant human fibronectin fragment enhanced infection of KG-1 cells by GaLV gp retrovirus (A). Infection rates of TZM-bl cells that have been added to RetroNectin® recombinant human fibronectin fragment or SWB coated and virus treated plates were further increased by a second infection using SWB treated HIV virus (B). Transduction rates of KG-1 cells that have been added to RetroNectin® recombinant human fibronectin fragment coated and lentiviral vector treated plates were further increased by a second transduction using SWB treated lentiviral vector (C).
Figure 14:
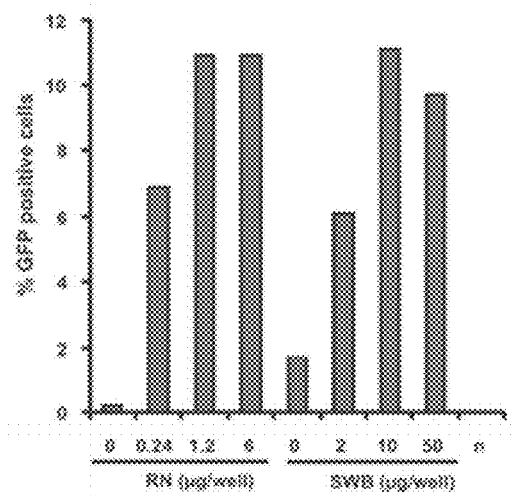
Figure 14:
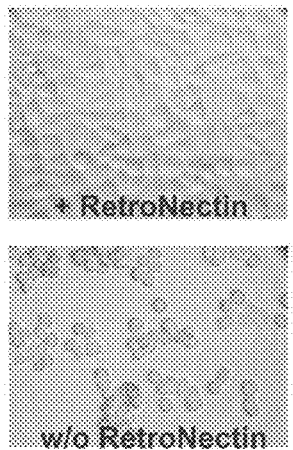
Figure 14:
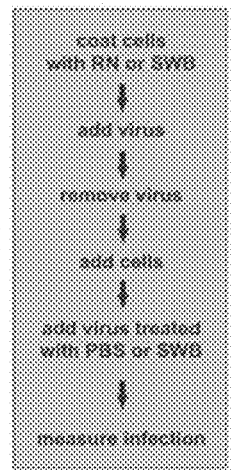
Figure 14:
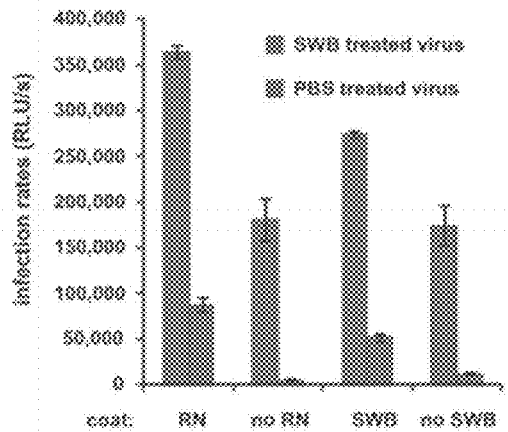
Figure 14:
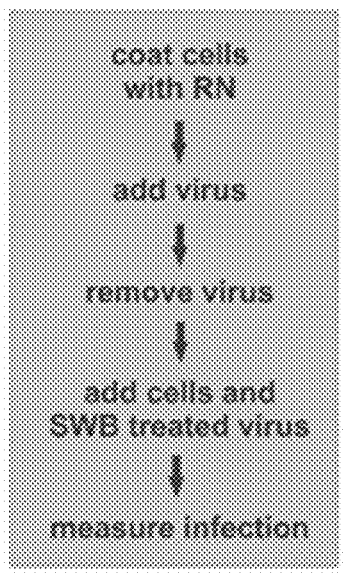
Figure 14:
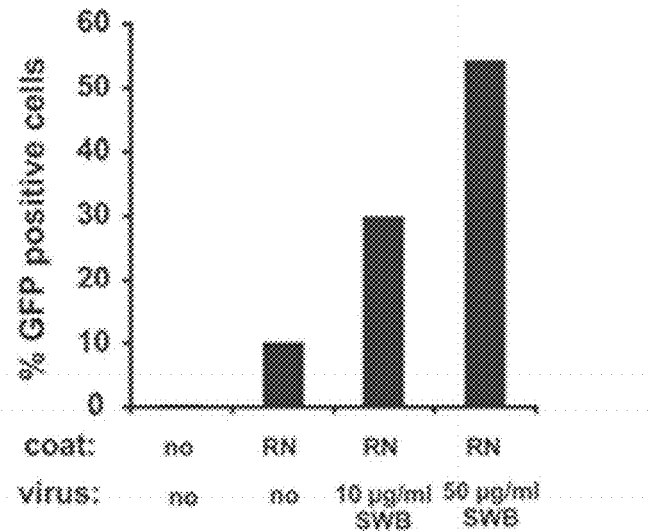

These data obtained with LV and RV particles carrying various glycoproteins show that SWB has a broad infection enhancing activity that is largely independent of the envelope glycoprotein. Thus, SWB is a highly useful tool to facilitate retro- and lentiviral gene transfer.

SWB Accelerated Transduction and Transgene Expression

To test if SWB might reduce the time needed to detect transgene expression, GaLV-gp pseudotyped retroviral particles (FIG. 9 G, H) and VSV-G pseudotyped retroviral particles (FIG. 9 I, K) were treated with SWB. The mixtures were used to inoculate HeLa cells and the rate of GFP positive cells and mean fluorescence intensities were determined after 1 to 4 days by FACS analyses. Arbitrary units were calculated by multiplying mean fluorescence intensities with % GFP positive cells and plotted against the SWB concentrations (FIG. 9 G, I), or against the day on which the FACS analysis has been performed (FIG. 9 H, K). As expected from the results described above, SWB dose-dependently enhanced HeLa transduction by both RV vector preparations. Interestingly, detectable rates of GFP expressing cells were observed already 2 days post transduction in cell cultures infected with SWB treated virus, whereas GFP signals in control experiments (no SWB) were close to those of uninfected cells (FIG. 9 H, K). Thus, SWB does not only increase the number of transduced cells but also accelerates viral entry and thus transgene expression allowing to reduce incubation times of viral stock solutions and cells.

The Ratio of SWB Volume to Virus Volume does not Affect Infectivity Enhancement

In most experiments 50% virus was mixed with 50% SWB (1/1). For most applications it might be useful to treat virus stocks directly by adding small volumes of SWB amyloid. To test this, R5 HIV was mixed with SWB in ratios of 1/1, 1/5 and 1/10 and used to infect TZM-bl indicator cells. The concentrations of SWB during virions treatment were similar. Infection rates determined 2 days later showed that SWB efficiently enhanced HIV infection irrespective of the mixing ratios of virus and peptide (FIG. 10). Thus, SWB can be added directly into the virus stock without markedly increasing the infection volume allowing minimizing infection volumes.

SWB Enhances Infection Rates by Virion and Cell Treatment

To test whether SWB promotes infection by interaction with the virion or the cell, SWB was either added directly to TZM-bl cells and subsequently infected with HIV-1, or HIV-1 particles were first treated with SWB in a small volume followed by infection of cells with this mixture in a larger volume. It was found that under both experimental conditions SWB was active (FIG. 11 A). When plotting the final cell culture concentrations of SWB on the x-axes, both graphs matched, suggesting that the important factor is the concentration of SWB in the presence of both, virions and cells (FIG. 11 A). These data suggest that SWB mediated infectivity enhancement is based on the interaction of amyloid with the virion and the cellular membrane thereby increasing viral attachment and thus infection rates. In this experiment, final concentrations of SWB exceeding 4 μM resulted in over infection of target cells and virus induced cytopathic effects, and hence reduced reporter gene activities.

SWB Mediated Virus Pull-Down and Concentration of Virus

It was previously shown that SEVI amyloid can be pelleted by centrifugation (Roan et al., 2009). Therefore, a similar experiment was performed with freshly prepared SWA and SWB (10 mg/ml DMSO stock diluted 50 fold in PBS) and preformed SEVI fibrils (control), respectively. The 200 μg/ml solutions were centrifuged, supernatants taken and pellets resuspended to the original volume in PBS. Both, pellets and supernatants were further diluted, mixed with virus and used to infect TZM-bl cells. Only the pelleted fractions of SWB and SEVI increased reporter gene expression whereas the respective supernatants lacked any virus enhancing activity demonstrating that the infectivity enhancing material of SWB (i.e. insoluble aggregates of SWB) is pelletable, (FIG. 12 A). Since SWB could be sedimented by centrifugation it was further tested, whether SWB could be used to co-sediment virus. To this end, R5 HIV was mixed with SWB or PBS and centrifuged for 5 min at various speeds. The supernatants (SN) were collected and the pellets (PE) resuspended, and both were used to infect TZM-bl cells. Gal screen assays performed 2 days later showed that high speed centrifugation of the SWB containing virus stock resulted in the recovery of ~85% of the total infectivity in the pellet (~1200,000 RLU/s), whereas the remaining supernatant just contained ~15% (~160,000 RLU/s) (FIG. 12 B). The PBS treated virus sample was less infectious and the pellet just contained ~50% of the total infectivity. The amount of infectious virus that was recovered in the pellet fraction decreased with reduced centrifugation speeds and inversely correlated with the infectivities of the supernatants (FIG. 12 B). These data show that insoluble aggregates of SWB allow to pull-down infectious HIV from a virus stock solution. One advantage of this approach is that metabolized old medium of the virus stock can be easily exchanged by fresh medium of choice. A second advantage is the possibility to easily concentrate virus by reconstituting pelleted virus in a lower volume than the original one. To test this, 1,000 μl of a PBS or SWB treated HIV stock was subjected to high speed centrifugation (or was not centrifuged at all). Afterwards, the supernatants (SN) were collected and the resulting pellets (PE) resuspended in 100 μl DMEM. The amount of HIV-1 in each fraction was determined by an HIV-1 p24 ELISA. The SWB precipitated pellet contained almost 1.2 μg capsid antigen whereas the pellet obtained by centrifugation of PBS treated virus contained less than 100 ng (FIG. 12 C). Thus, SWB does not only allow to precipitate virus from a virus solution but also to increase the virus concentration by one centrifugation step. Finally, the reconstituted virus is already associated with SWB and thus more infectious.

To test whether SWB also allows pelleting retroviral vectors, RV-GFP particles were mixed with either PBS or various concentrations of SWB and subsequently centrifuged (5 min at 21,000g). Supernatants (SN) were collected and pellets (PE) reconstituted in the original volume with fresh medium. Thereafter KG-1 cells were transduced. FACS analyses revealed that high speed centrifugation (21,000 g) completely pelleted SWB and the associated RV vector since only the pellet fraction efficiently enhanced transduction (FIG. 12 D).

SWB Coated to Culture Dishes Captures Virus and Enhances Infection

To test if SWB, like RetroNectin® recombinant human fibronectin fragment, enhances viral infection when coated on the surface of cell culture dishes, four microtiter plates obtained from different providers (A: Thermo Scientific NuncTM Nunc F96 MicroWell™ Plates Polystyrene Clear No.:167008; B: Thermo Scientific NuncTM Nunc F96 MicroWell™ Plates Polystyrene Clear No.: 442404; C: CORNING (96 well) EIA/RIA Flat Bottom, High Bind, Non-sterile No.: 3590; D: CORNING (96-Well) Multiple Well Cluster Plate TC Treated No.: 3596) were incubated with freshly diluted SWB. The next day, the solutions were removed and HIV-1 added. After 4 hrs of incubation, the virus inoculum was removed and TZM-bl indicator cells were added. In some control samples, the virus inoculum has not been removed and cells were directly added to the virus containing wells (ctrl). Gal Screen assays performed 2 days later showed that infection rates of cells added to SWB coated plates were strongly increased (FIG. 13 A). Maximum enhancement was observed for all 4 dishes between 1-10 µg SWB per well (FIG. 13 A). Importantly, infection rates observed in control samples (in which the virus inoculum has not been removed and in which target cells were thus exposed to the total amount of input virus throughout the experiment) were even lower than those observed in wells that were coated with SWB and where the whole inoculum has been removed (FIGS. 13 A and B). Similar experiments performed with HIV-1 and CEMxM7 showed that coated SWB also increased infection rates of suspension cells (FIG. 13 C), irrespective if SWB containing wells were washed or not before adding cells. Since the previous results have been obtained with a replication competent lentivirus it was further tested, whether coated SWB also favours transduction rates of a VSV-G pseudotyped RV vector. As expected, SWB coated onto plates obtained from two different manufacturers increased the efficiency of RV/VSV-G mediated GFP transfer into HeLa cells by more than 7 fold (FIG. 13 D). In summary these data show that SWB can be coated onto the surfaces of cell culture dishes allowing to increases viral infection rates. SWB mediated capture of virions also allows to remove metabolized medium of the virus stock and to exchange it with fresh medium optimized for subsequent cell culture conditions. In summary the data demonstrate that SWB coated on the surfaces of cell culture plates significantly enhances lentiviral and retroviral mediated gene transduction into mammalian cells.

SWB Enhances Viral Infectivity in Suspension

SWB can increase transduction rates when added directly to virus stock solutions or to cells. To compare the modes of action of RetroNectin® recombinant human fibronectin fragment and SWB, lentiviral particles were treated with both enhancers in a relatively small volume and used to infect larger cell cultures. HIV-1 virus stocks containing 1 and 0.1 ng p24 antigen were incubated with 0.0, 0.8, 4, or 20 pg/ml enhancer and used to infect TZM-bl cells. As expected, SWB strongly enhanced infection whereas treatment of virus stocks with RetroNectin® recombinant human fibronectin fragment had no effect (FIG. 11 B). Additionally, the activities of SWB and RetroNectin® recombinant human fibronectin fragment were compared under conditions in which the target cells were incubated first followed by infection with HIV-1. TZM-bl cells were incubated with 0.0, 0.8, 4, or 20 μg/ml enhancer and subsequently infected with R5 HIV. Also under these conditions, SWB potently favoured infection whereas levels of infection in cells treated with RetroNectin® recombinant human fibronectin fragment were comparable to those not treated by any enhancer (FIG. 11 C), indicating that SWB and RetroNectin® recombinant human fibronectin fragment boosts viral infection by different mechanisms. In sum these results demonstrate that in contrast to RetroNectin® recombinant human fibronectin fragment that is active only if bound on surfaces, SWB potently enhanced viral infection when added to virions directly, or when used for treating target cells before infection. These properties render SWB a highly useful tool to improve gene transfer rates by retroviral transductions.

Cell Culture Dish Coated SWB and RetroNectin® Increases Transduction with Similar Efficiencies To compare the infection enhancing properties of SWB and RetroNectin® recombinant human fibronectin fragment, the inventors tested their effects on promoting retroviral (RV) transduction rates into the stem cell like KG-1 cells in a site by site approach. Therefore, microtiter plates from BD plates (#351172) recommended by Takara for the work with RetroNectin® recombinant human fibronectin fragment were coated with the compound and routinely used microtiter plates from Costar (Corning® 96 Well Clear Flat Bottom Polystyrene Tissue Culture (TC)Treated Microplates; Costar #3596) with SWB, respectively. Both plates were then incubated with similar amounts of a GaLV glycoprotein (GaLV gp) pseudotyped retroviral vector (GaLV RV) for 4 hrs. RetroNectin® recombinant human fibronectin fragment coated microplates were washed as recommended by the manufacturer and SWB coated microplates were washed with 100 μl PBS. Thereafter, KG-1 cells were plated and the transduction rates were measured by FACS analysis. The results showed that both compounds dose dependently increased the rate of GFP expressing cells to a maximum of ~11% (FIG. 14 A). This value was reached in the presence of 1.2 μg RetroNectin® recombinant human fibronectin fragment or 10 μg SWB per well (FIG. 14 A). A further increase in the amounts of any of the enhancers did not result in higher transduction rates, suggesting a low vector titer as limiting factor. Interestingly, transduction rates in the absence of RetroNectin® recombinant human fibronectin fragment in BD microtiter plates were lower than those in the absence of SWB in TC treated Costar plates (FIG. 14 A, compare 0 on x-axes), suggesting that cell growth in BD plates might be compromised. Indeed, control experiments performed in BD plates (#351172) revealed that in the absence of RetroNectin® recombinant human fibronectin fragment adherent HeLa cells did not attach efficiently resulting in round shaped cells that did not grow with normal kinetics (FIG. 14 A, right panel), likely explaining the reduced susceptibility to infection observed before. Thus, when analyzed under these conditions, the transduction enhancing effect of RetroNectin® recombinant human fibronectin fragment is likely to be overestimated since at least in part this effect is mediated by a cellular attachment function that is normally mediated by appropriate coating of standard cell culture plates.

A Combination of RetroNectin and SWB Allows Most Efficient Infection and Transduction In addition the inventors tested if a combination of RetroNectin® recombinant human fibronectin fragment and SWB allows for a more efficient lentiviral infection compared to both enhancers alone. Therefore, BD microtiter plates (above) were coated with 6 μg/well RetroNectin® recombinant human fibronectin fragment and 10 μg/ml SWB. The next day, HIV-1 was added, the inoculum removed and CEMM7 indicator cells added. Thereafter, the same amount of virus, either treated with SWB (10 μg/ml) or PBS was added. Luciferase assays performed two days later showed that infection of RetroNectin® recombinant human fibronectin fragment coated wells with SWB treated virus resulted in highest reporter gene activities (FIG. 14 B) suggesting that the combination of both enhancers yields highest infection rates. To confirm these data using a lentiviral vector system, BD plates were coated with RetroNectin® recombinant human fibronectin fragment and incubated with a lentiviral, GaLV pseudotyped vector. Thereafter KG-1 cells were added and subsequently infected with a similar volume of PBS or SWB treated virus that has been used before. FACS analyses performed 3 days later showed that ~10% of the cells were transduced in wells coated with RN and infected with untreated virus, but more than 50% of the cells were GFP positive when SWB treated viral vector was added. Thus, combining both approaches might yield highest rates of transduction.

REFERENCES

Brender J R, Hartman K, Gottler L M, Cavitt M E, Youngstrom D W, Ramamoorthy A. Helical conformation of the SEVI precursor peptide PAP248-286, a dramatic enhancer of HIV infectivity, promotes lipid aggregation and fusion. Biophys J. 2009 Nov. 4; 97(9):2474-83.

Gurgo C, Guo H G, Franchini G, Aldovini A, Collalti E, Farrell K, Wong-Staal F, Gallo R C, Reitz M S Jr. Envelope sequences of two new United States HIV-1 isolates. Virology. 1988 June; 164(2):531-6.

Münch J, Rücker E, Ständker L, Adermann K, Goffinet C, Schindler M, Wildum S, Chinnadurai R, Rajan D, Specht A, Giménez-Gallego G, Sánchez P C, Fowler D M, Koulov A, Kelly J W, Mothes W, Grivel J C, Margolis L, Keppler O T, Forssmann W G, Kirchhoff F. Semen-derived amyloid fibrils drastically enhance HIV infection. Cell. 2007 Dec. 14; 131(6):1059-71

Papkalla A, Münch J, Otto C, Kirchhoff F. Nef enhances human immunodeficiency virus type 1 infectivity and replication independently of viral coreceptor tropism. J. Virol. 2002 August; 76(16):8455-9.

Roan N R, Münch J, Arhel N, Mothes W, Neidleman J, Kobayashi A, Smith-McCune K, Kirchhoff F, Greene W C. The cationic properties of SEVI underlie its ability to enhance human immunodeficiency virus infection. J. Virol. 2009 January; 83(1):73-80. Epub 2008 Oct. 22.

Roan N R, Sowinski S, Münch J, Kirchhoff F, Greene W C. Aminoquinoline surfen inhibits the action of SEVI (semen-derived enhancer of viral infection). J Biol. Chem. 2010 Jan. 15; 285(3):1861-9. Epub 2009 Nov. 6.

Wurm M, Schambach A, Lindemann D, Hanenberg H, Ständker L, Forssmann W G, Blasczyk R, Horn P A. The influence of semen-derived enhancer of virus infection on the efficiency of retroviral gene transfer. J Gene Med. 2010 February; 12(2):137-46.

The invention claimed is:

1. An isolated peptide comprising SEQ ID NO: 1, wherein the isolated peptide has between 12 to 25 amino acids.

2. An isolated peptide comprising SEQ ID NO: 2, wherein the isolated peptide has between 11 to 25 amino acids.

3. The isolated peptide of claim 1, wherein the isolated peptide has 20 amino acids.

4. The isolated peptide of claim 2, wherein the isolated peptide has 20 amino acids.

5. The isolated peptide of claim 1, wherein the peptide is soluble in an organic solvent.

6. The isolated peptide of claim 2, wherein the peptide is soluble in an organic solvent.

7. A kit comprising the peptide of claim 1.

8. A kit comprising the peptide of claim 2.

9. The isolated peptide of claim 5, wherein the organic solvent comprises an organosulfur compound.

10. The isolated peptide of claim 6, wherein the organic solvent comprises an organosulfur compound.

11. The isolated peptide of claim 9, wherein the organosulfur compound is dimethylsulfoxide (DMSO).

12. The isolated peptide of claim 10, wherein the organosulfur compound is dimethylsulfoxide (DMSO).

* * * * *

```
SEQUENCE LISTING

<160> NUMBER OF SEQ ID NOS: 13

<210> SEQ ID NO 1
<211> LENGTH: 12
<212> TYPE: PRT
<213> ORGANISM: Artificial Sequence
<220> FEATURE:
<223> OTHER INFORMATION: SW-peptide derived from peptide gp120 of HIV-1
      strain MN (Gurgo et al., 1988)

<400> SEQUENCE: 1

Gln Cys Lys Ile Lys Gln Ile Ile Asn Met Trp Gln
1               5                   10

<210> SEQ ID NO 2
<211> LENGTH: 11
<212> TYPE: PRT
<213> ORGANISM: Artificial Sequence
<220> FEATURE:
<223> OTHER INFORMATION: SW-peptide derived from peptide gp120 of HIV-1
      strain MN (Gurgo et al., 1988)

<400> SEQUENCE: 2

Gln Cys Lys Ile Lys Gln Ile Ile Asn Met Trp
1               5                   10

<210> SEQ ID NO 3
<211> LENGTH: 19
<212> TYPE: PRT
<213> ORGANISM: Artificial Sequence
<220> FEATURE:
<223> OTHER INFORMATION: SW-peptide derived from peptide gp120 of HIV-1
      strain MN (Gurgo et al., 1988)

<400> SEQUENCE: 3

Asn Ile Thr Leu Gln Cys Lys Ile Lys Gln Ile Ile Asn Met Trp Gln
1               5                   10                  15

Glu Val Gly
```

```
<210> SEQ ID NO 4
<211> LENGTH: 10
<212> TYPE: PRT
<213> ORGANISM: Artificial Sequence
<220> FEATURE:
<223> OTHER INFORMATION: SW-peptide derived from peptide gp120 of HIV-1
      strain MN (Gurgo et al., 1988)

<400> SEQUENCE: 4

Gln Ile Ile Asn Met Trp Gln Glu Val Gly
1               5                   10

<210> SEQ ID NO 5
<211> LENGTH: 19
<212> TYPE: PRT
<213> ORGANISM: Artificial Sequence
<220> FEATURE:
<223> OTHER INFORMATION: SW-peptide derived from peptide gp120 of HIV-1
      strain MN (Gurgo et al., 1988)

<400> SEQUENCE: 5

Thr Ile Thr Leu Pro Cys Arg Ile Lys Gln Phe Ile Asn Met Trp Gln
1               5                   10                  15

Glu Val Gly

<210> SEQ ID NO 6
<211> LENGTH: 4
<212> TYPE: PRT
<213> ORGANISM: Artificial Sequence
<220> FEATURE:
<223> OTHER INFORMATION: SW-peptide derived from peptide gp120 of HIV-1
      strain MN (Gurgo et al., 1988)

<400> SEQUENCE: 6

Ile Asn Met Trp
1

<210> SEQ ID NO 7
<211> LENGTH: 6
<212> TYPE: PRT
<213> ORGANISM: Artificial Sequence
<220> FEATURE:
<223> OTHER INFORMATION: SW-peptide derived from peptide gp120 of HIV-1
      strain MN (Gurgo et al., 1988)
<220> FEATURE:
<221> NAME/KEY: misc_feature
<222> LOCATION: (2)..(2)
<223> OTHER INFORMATION: Xaa can be any naturally occurring amino acid

<400> SEQUENCE: 7

Gln Xaa Ile Asn Met Trp
1               5

<210> SEQ ID NO 8
<211> LENGTH: 9
<212> TYPE: PRT
<213> ORGANISM: Artificial Sequence
<220> FEATURE:
<223> OTHER INFORMATION: SW-peptide derived from peptide gp120 of HIV-1
      strain MN (Gurgo et al., 1988)

<400> SEQUENCE: 8

Asn Ile Thr Leu Gln Cys Lys Ile Lys
1               5

<210> SEQ ID NO 9
<211> LENGTH: 6
<212> TYPE: PRT
<213> ORGANISM: Artificial Sequence
```

```
<220> FEATURE:
<223> OTHER INFORMATION: SW-peptide derived from peptide gp120 of HIV-1
      strain MN (Gurgo et al., 1988)

<400> SEQUENCE: 9

Gln Cys Lys Ile Lys Gln
1               5

<210> SEQ ID NO 10
<211> LENGTH: 3
<212> TYPE: PRT
<213> ORGANISM: Artificial Sequence
<220> FEATURE:
<223> OTHER INFORMATION: SW-peptide derived from peptide gp120 of HIV-1
      strain MN (Gurgo et al., 1988)

<400> SEQUENCE: 10

Lys Ile Lys
1

<210> SEQ ID NO 11
<211> LENGTH: 10
<212> TYPE: PRT
<213> ORGANISM: Artificial Sequence
<220> FEATURE:
<223> OTHER INFORMATION: SW-peptide derived from peptide gp120 of HIV-1
      strain MN (Gurgo et al., 1988)

<400> SEQUENCE: 11

Lys Ile Lys Gln Ile Ile Asn Met Trp Gln
1               5                   10

<210> SEQ ID NO 12
<211> LENGTH: 19
<212> TYPE: PRT
<213> ORGANISM: Artificial Sequence
<220> FEATURE:
<223> OTHER INFORMATION: SW-peptide derived from peptide gp120 of HIV-1
      strain MN (Gurgo et al., 1988)

<400> SEQUENCE: 12

Thr Ile Thr Leu Pro Cys Arg Ile Lys Gln Ile Ile Asn Met Trp Gln
1               5                   10                  15

Gly Val Gly

<210> SEQ ID NO 13
<211> LENGTH: 32
<212> TYPE: PRT
<213> ORGANISM: Homo sapiens

<400> SEQUENCE: 13

Ser Asn Asn Asn Ile Thr Leu Gln Cys Lys Ile Lys Gln Ile Ile Asn
1               5                   10                  15

Met Trp Gln Glu Val Gly Lys Ala Met Tyr Ala Pro Pro Ile Glu Gly
            20                  25                  30
```